(12) United States Patent
Sagane et al.

(10) Patent No.: US 8,309,792 B2
(45) Date of Patent: Nov. 13, 2012

(54) NON-HUMAN GENE-DISRUPTED ANIMAL WITH DISRUPTED ADAM11 GENE

(75) Inventors: Koji Sagane, Ibaraki-Ken (JP); Eiki Takahashi, Chiba-Ken (JP); Kazuto Yamazaki, Ibaraki-Ken (JP); Turo Oki, Ibaraki-Ken (JP)

(73) Assignee: Eisai R&D Management Co., Ltd., Tokyo-To (JP)

( * ) Notice: Subject to any disclaimer, the term of this patent is extended or adjusted under 35 U.S.C. 154(b) by 1068 days.

(21) Appl. No.: 11/988,619

(22) PCT Filed: Jul. 12, 2006

(86) PCT No.: PCT/JP2006/313862
§ 371 (c)(1),
(2), (4) Date: Jan. 11, 2008

(87) PCT Pub. No.: WO2007/007787
PCT Pub. Date: Jan. 18, 2007

(65) Prior Publication Data
US 2010/0333216 A1 Dec. 30, 2010

(30) Foreign Application Priority Data
Jul. 13, 2005 (JP) .................................. 2005-204841

(51) Int. Cl.
*A01K 67/027* (2006.01)
*C12N 15/00* (2006.01)
*G01N 30/00* (2006.01)

(52) U.S. Cl. ................. 800/18; 800/21; 800/3; 435/325
(58) Field of Classification Search .................... 800/18, 800/21, 3; 435/325
See application file for complete search history.

(56) References Cited

FOREIGN PATENT DOCUMENTS

| | | |
|---|---|---|
| JP | 2000-93043 A | 4/2000 |
| WO | 02/079420 | 10/2002 |
| WO | WO 02/079420 * | 10/2002 |

OTHER PUBLICATIONS

Takahashi et al. (Feb. 2006) BMC Neuroscience, vol. 7, article 19 (11 pages).*
Sagane et al. (1999) Gene, vol. 236, 79-86.*
Rybnikova et al. (2002) Neuroscience, vol. 112(4), 921-934.*
Wigley et al. (1994) Reprod. Fertil. Dev., vol. 6, 585-588.*
Mullins et al. (1996) J. Clin. Invest., vol. 98(11), S37-S40.*
Wall (1996) Theriogenology, vol. 45, 57-68.*
Campbell et al. (1997)Theriogenology, vol. 47 (1), 63-72.*
Sagane et al., "Cloning and chromosomal mapping of mouse ADAM11, ADAM22 and ADAM23", Gene, vol. 236, No. 1, pp. 79-86, 1999.
Capecchi, "Altering the Genome by Homologous Recombination", Science, vol. 244, No. 4910, pp. 1228-1292, 1989.
Rybnikova et al., "Developmental regulation and neuronal expression of the cellular disintegrin adam11 gene in mouse nervous system", Neuroscience, vol. 112, No. 4, pp. 921-934, 2002.
International Preliminary Report on Patentability from International Application No. PCT/JP2006/313862, dated Jan. 16, 2008 (date of issue of report).
Translation of Written Opinion from International Application No. PCT/JP2006/313862, dated Sep. 4, 2008 (date of issue of report).
Office Action from Japan Patent Application No. 2007-524676, dated Mar. 13, 2012. Translation enclosed.
Amendment from Japanese Patent Application No. 2007-524676, filed May 24, 2012. Translation included.
Notice of Appeal from Japanese Patent Application No. 2007-524676, filed May 24, 2012. Translation included.
Sagane, K., et al., Biochemical Journal, The Biochemical Society, London, 334(01); 93-98, (1998).
Takahashi, Eiki, et al., BMC Neuroscience, Biomed Central, London, GB, 7(1); 19, (2006).
Supplementary European Search Report, EP 06 768 126, Oct. 9, 2008.

* cited by examiner

*Primary Examiner* — Anne Marie S Wehbe
(74) *Attorney, Agent, or Firm* — Clark & Elbing LLP

(57) ABSTRACT

It is an object of the present invention to provide a non-human gene-disrupted animal with a disrupted ADAM11 gene. According to the present invention, a non-human gene-disrupted animal, wherein either one of or both alleles of an ADAM11 gene are disrupted, is provided.

9 Claims, 11 Drawing Sheets

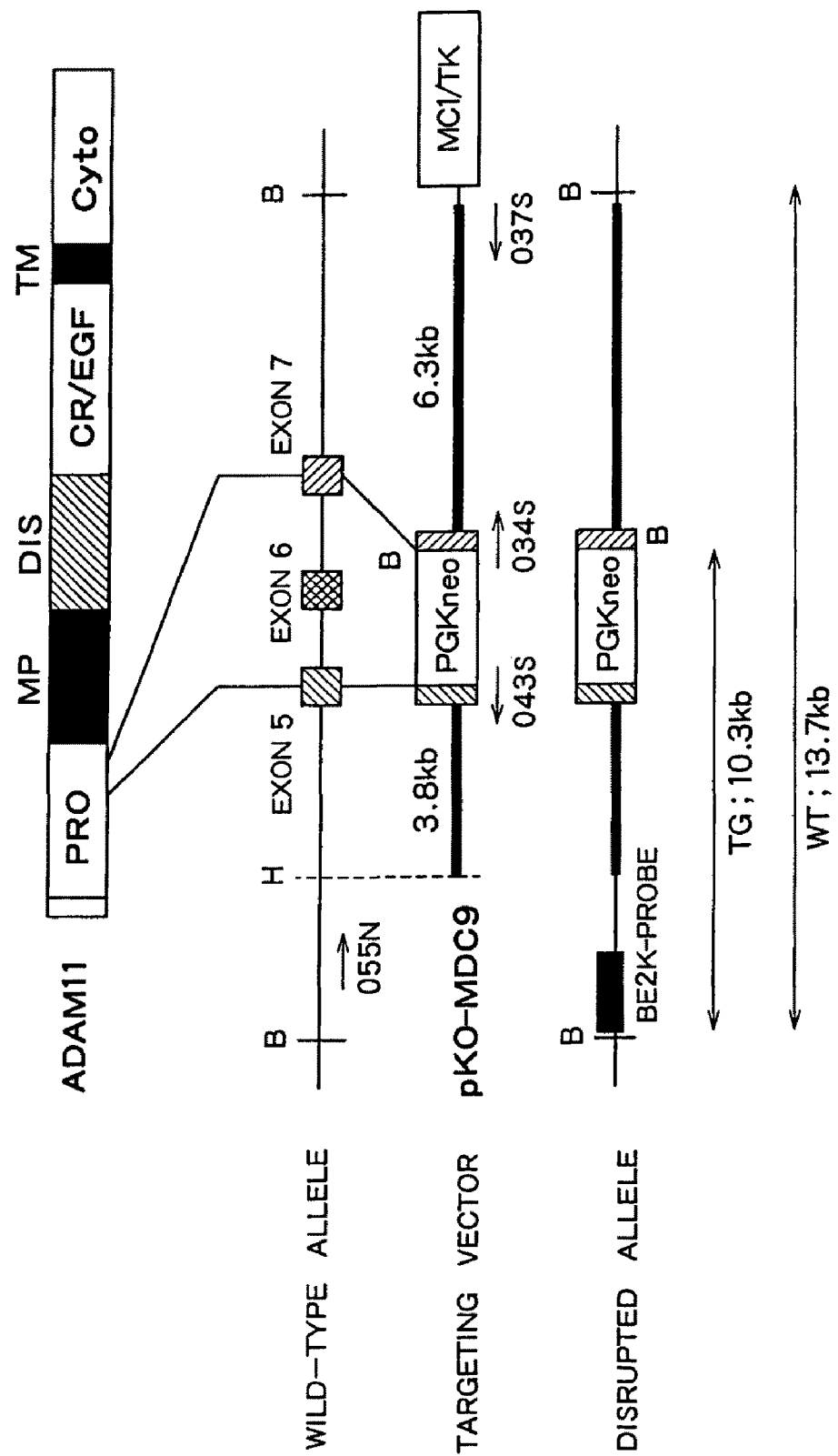
F I G. 1

NON-HUMAN GENE-DISRUPTED ANIMAL WITH DISRUPTED ADAM11 GENE

TECHNICAL FIELD

The present invention relates to a non-human gene-disrupted animal produced by disrupting an ADAM11 gene and a use thereof.

BACKGROUND OF THE INVENTION

ADAM (A Disintegrin and Metalloprotease) is a generic name for a single transmembrane protein having two characteristic domain structures, namely, a disintegrin-like domain and a metalloprotease-like domain. In 1992, Blobel et al. succeeded in the cloning of ADAM1 (Fertilin α) and ADAM2 (Fertilin β) (Blobel C. P., Wolfsberg T. G. et al., (1992). Nature. 356: 248-252). Thereafter, their paralogs have been successively cloned. As a result, at present, it has been clarified that such ADAM genes form an enormous family consisting of approximately 30 species.

Disintegrin is a peptide having the ability to inhibit blood coagulation, which is contained in the hemolytic snake venom of *Trimeresurus flavoviridis* (habu), rattlesnake, etc. It has been known that disintegrin inhibits the binding of integrin αIIbβ3 to fibrinogen on a thrombocyte. The amino acid sequence of a disintegrin-like domain of the ADAM family has high homology with that of snake venom disintegrin. As a matter of fact, it has been reported that several types of ADAM proteins bind to integrin (Judith M White. (2003). Cell Biology 15: 598-606).

Another characteristic domain, metalloprotease-like domain, has high homology at the amino acid sequence level with snake venom metalloprotease or matrix metalloprotease. Thus, the metalloprotease-like domain is expected to function as a protease. In fact, it has been reported that several ADAM proteins have protease activity (D. F. Seals and S. A. Courtneidge (2003). Genes & Development 17: 7-30). However, approximately half of ADAM genes do not have a zinc-binding motif (HEXXHXXGXXH) that is considered essential for metalloprotease activity, and thus it is considered that such ADAM genes do not have protease activity.

Taking into consideration these characteristic domain structures, it is considered that the ADAM protein has two functions, namely, a function to recognize a specific integrin and a function to specifically process a substrate protein. It is considered that some ADAM proteins have both of the two functions and that the other ADAM proteins have either one function. In addition, it has been reported that such an ADAM protein is produced in the form of a precursor, and that when a Pro domain (proprotein domain) is cleaved, the ADAM protein is expressed on the surface of a cell.

To date, the full-length sequence of an ADAM11 gene belonging to the ADAM family has been determined, and it has been reported that the ADAM 11 gene is a breast cancer inhibiting gene (Japanese Patent Laid-Open Publication No. 330799/1995). Many ADAM family genes are expressed specifically in germ-line tissues, or are expressed in a wide range of tissues. In contrast, it has been confirmed that the ADAM11 gene is highly expressed specifically in nervous system tissues (Sagane K., Ohya Y, et al., (1998). Biochem J 334: 93-98). However, specific functions of the ADAM11 gene towards nervous system tissues have not been reported.

SUMMARY OF THE INVENTION

The present inventors have produced a mouse whose ADAM11 gene has been knocked out and then found that such a knockout mouse exhibits the character of a nerve-related disease. The present invention is based on such findings.

The present invention provides a non-human gene-disrupted animal produced by disrupting both or either one of alleles of an ADAM11 gene and a progeny thereof (hereinafter referred to as "the non-human gene-disrupted animal of the present invention").

Among the non-human gene-disrupted animals of the present invention, a gene-disrupted animal whose both alleles of the ADAM11 gene have been disrupted (a first embodiment) has the inactivated ADAM11 gene and exhibits the character of a nerve-related disease.

Accordingly, the non-human gene-disrupted animal in the first embodiment of the present invention is useful for the clarification of the mechanism of disease with which the ADAM11 is associated and the searching and development of a substance useful for the treatment of a nerve-related disease.

In addition, a gene-disrupted animal whose either one allele of the ADAM11 gene has been disrupted (a second embodiment) can be subjected to crossing, so as to obtain the gene disrupted animal whose both alleles of the ADAM11 gene have been disrupted (the first embodiment). Accordingly, the non-human gene-disrupted animal in the second embodiment of the present invention is useful as a parent animal used to produce the gene-disrupted animal in the first embodiment.

Specifically, the present invention is as follows:

(1) A non-human gene-disrupted animal or a progeny thereof, wherein both alleles of an ADAM11 gene are disrupted.

(2) The non-human gene-disrupted animal or a progeny thereof according to (1) above, wherein both alleles of the ADAM11 gene are disrupted by substituting the entire or a part of both alleles of the ADAM11 gene with a foreign sequence.

(3) The non-human gene-disrupted animal or a progeny thereof according to (1) or (2) above, which has a phenotype causing the development of a nerve-related disease.

(4) The non-human gene-disrupted animal or a progeny thereof according to (3) above, wherein the nerve-related disease is incoordination, memory disorder, agnosia, learning disability, or paralgesia.

(5) A non-human gene-disrupted animal or a progeny thereof, wherein either one allele of an ADAM11 gene is disrupted.

(6) The non-human gene-disrupted animal or a progeny thereof according to (5) above, wherein either one allele of the ADAM11 gene is disrupted by substituting the entire or a part of the allele of the ADAM11 gene with a foreign sequence.

(7) The non-human gene-disrupted animal or a progeny thereof according to any one of (1) to (6) above, wherein the non-human animal is a rodent.

(8) The non-human gene-disrupted animal or a progeny thereof according to (7) above, wherein the rodent is a mouse.

(9) A tissue obtained from the non-human gene-disrupted animal or a progeny thereof according to any one of (1) to (8) above.

(10) An animal cell obtained from the non-human gene-disrupted animal or a progeny thereof according to any one of (1) to (8) above.

(11) A breeding material obtained from the non-human gene-disrupted animal or a progeny thereof according to any one of (1) to (8) above.

(12) A method for producing the non-human gene-disrupted animal according to any one of (5) to (8) above, wherein either one allele of the ADAM11 gene is disrupted, comprising the following steps:
  (a) transforming non-human animal embryonic stem cells (ES cells) with a polynucleotide containing a disrupted ADAM11 gene;
  (b) selecting an ES cell, into the genome of which the above described polynucleotide has been incorporated;
  (c) introducing the selected ES cell into a non-human animal embryonic cell;
  (d) transplanting the ES cell-introduced non-human animal embryonic cell to the reproductive organ of a wild-type pseudopregnant non-human female animal to reproduce a chimeric animal; and
  (e) crossing the obtained chimeric animal with a wild-type non-human animal to reproduce a non-human gene-disrupted animal wherein either one allele of the ADAM11 gene is disrupted.

(13) A method for producing the non-human gene-disrupted animal according to any one of (1) to (4), (7), and (8) above, wherein both alleles of the ADAM11 gene are disrupted, comprising the following steps:
  (a) transforming non-human animal embryonic stem cells (ES cells) with a polynucleotide containing a disrupted ADAM11 gene;
  (b) selecting an ES cell, into the genome of which the above described polynucleotide has been incorporated;
  (c) introducing the selected ES cell into a non-human animal embryonic cell;
  (d) transplanting the ES cell-introduced non-human animal embryonic cell to the reproductive organ of a wild-type pseudopregnant non-human female animal, so as to reproduce a chimeric animal;
  (e) crossing the obtained chimeric animal with a wild-type non-human animal to reproduce a non-human gene-disrupted animal wherein either one allele of the ADAM11 gene is disrupted; and
  (f) crossing a male of the obtained non-human gene-disrupted animals with a female of the obtained non-human gene-disrupted animals to reproduce a non-human gene-disrupted animal wherein both alleles of the ADAM11 gene are disrupted.

(14) A method for screening for a substance used in the treatment of a nerve-related disease, a salt thereof, or a solvate thereof, comprising the following steps:
  (i) measuring the severity of a symptom of the nerve-related disease of the non-human gene-disrupted animal according to any one of (1) to (4), (7), and (8) above, wherein both alleles of the ADAM11 gene are disrupted;
  (ii) administering a test substance to the above described non-human gene-disrupted animal; and
  (iii) measuring the severity of a symptom of the nerve-related disease of the above described non-human gene-disrupted animal after administration of the test substance.

(15) The screening method according to (14) above, which further comprises the following step after step (iii):
  (iv) comparing the severity of a symptom of the nerve-related disease before administration of the test substance with the severity of a symptom of the nerve-related disease after administration of the test substance.

(16) The screening method according to (14) or (15) above, wherein the nerve-related disease is incoordination, memory disorder, agnosia, learning disability, or paralgesia.

(17) A pharmaceutical composition for use in the treatment of a nerve-related disease caused by inactivation of an ADAM11 gene, which comprises an ADAM11 protein.

(18) Use of an ADAM11 protein for the manufacture of a medicament for use in the treatment of a nerve-related disease caused by inactivation of an ADAM11 gene.

(19) A method for treating a nerve-related disease caused by inactivation of an ADAM11 gene, which comprises the step of administering to a mammal a therapeutically effective amount of the ADAM11 protein.

(20) A gene therapy agent for use in the treatment of a nerve-related disease caused by inactivation of an ADAM11 gene, which comprises a gene transfer vector to which the ADAM11 gene is operably linked.

(21) Use of a gene transfer vector to which an ADAM11 gene is operably linked for the manufacture of a gene therapy agent for use in the treatment of a nerve-related disease caused by inactivation of the ADAM11 gene.

(22) A method for treating a nerve-related disease caused by inactivation of an ADAM11 gene, which comprises the step of administering to a mammal the ADAM11 gene or a gene transfer vector to which the ADAM11 gene is operably linked.

BRIEF DESCRIPTION OF THE DRAWINGS

FIG. 1 shows the structure of a targeting vector.

DETAILED DESCRIPTION

ADAM11 Gene

Figure 2:
FIG. 2 shows the Southern blot analysis performed for selecting a homologous recombinant clone.

Any type of ADAM11 gene can be used, as long as it exists in autosomal genome and it can be transcribed to generate mRNA encoding an ADAM11 protein. Examples of such an ADAM11 gene include a genomic gene encoding the ADAM11 protein and cDNA encoding the ADAM11 protein.

The ADAM11 gene disrupted in the gene-disrupted animal of the present invention has been found in a human and a mouse. The following publications and accession numbers to database disclose the DNA sequences of such a human and a mouse, respectively:

Human: Japanese Patent Laid-Open Publication No. 330799/1995; GenBank: AB009675 (SEQ ID NO: 1)

Mouse: Sagane K. et al., Gene 1999 Aug. 5, 236(1): 79-86; GenBank: AB009676 (SEQ ID NO: 3)

With regard to a rat, a canine, and a chimpanzee, sequences estimated from the genomic sequences thereof by computer analysis have been registered on database as shown below. Such sequences can also be used:

Rat: Genbank#XM_340916

Dog: Genbank#XM_537616

Chimpanzee: Genbank#XM_511556

Long-tailed cock: Genbank#XM_425842

Even with regard to animals other than the aforementioned animals, persons skilled in the art can specify the sequence of the ADAM11 genes of such animals based on the full-length sequences of the known ADAM11 genes. That is, homology searching may be conducted based on the ADAM11 gene of a human or a mouse, and the ADAM11 gene of such an animal may be searched and specified. For such homology searching, BLAST as described later or the like can be used.

Examples of such an ADAM 11 gene include a gene encoding a human ADAM11 protein having the amino acid sequence as shown in SEQ ID NO: 2 and a gene encoding a mouse ADAM11 protein having the amino acid sequence as shown in SEQ ID NO: 4.

The ADAM11 gene to be disrupted in the gene-disrupted animal of the present invention includes a gene encoding a certain protein that is functionally equivalent to the ADAM11 protein. The term "functionally equivalent" is used herein to mean that substantially the same levels of normal functions (e.g., coordinated movement, memory, cognition, learning, or somatic sense (pain sense)) of the cerebral nervous system can be maintained. Whether or not it is "functionally equivalent" can be determined by comparing a non-human gene-disrupted animal that includes homozygous disruption of the gene with a normal non-human animal, and then evaluating whether or not substantially the same levels of normal functions (e.g., coordinated movement, memory, cognition, learning, or somatic sense (pain sense)) of a cerebral nervous system can be maintained. That is, when the normal functions of the cerebral nervous system of a non-human gene-disrupted animal including homozygous disruption of the gene were decreased or lost, it could be determined that the aforementioned gene is functionally equivalent to the ADAM11 gene. For such determination, a rotor rod test, a water maze test, a formalin test, an acetic acid rising method test, etc. can be used.

Moreover, when a gene encoding the amino acid sequence (e.g., the amino acid sequence as shown in SEQ ID NO: 2 or SEQ ID NO: 4) is a polymorphism, such a polymorphism is also included in such a protein that is functionally equivalent to the ADAM11.

Examples of a gene encoding a protein functionally equivalent to the ADAM11 protein include the following genes:

- a gene encoding an amino acid sequence (modified amino acid sequence) having an insertion, substitution or deletion of one or more amino acids, or addition of such amino acids to either one or both termini, with respect to the amino acid sequence of the ADAM11 protein (e.g., the amino acid sequence as shown in SEQ ID NO: 2 or SEQ ID NO: 4);
- a gene hybridizing with a gene encoding the amino acid sequence of the ADAM11 protein (e.g., the amino acid sequence as shown in SEQ ID NO: 2 or SEQ ID NO: 4) under stringent conditions; and
- a gene encoding an amino acid sequence having at least 70% identity with the amino acid sequence of the ADAM11 protein (e.g., the amino acid sequence as shown in SEQ ID NO: 2 or SEQ ID NO: 4).

In the specification of the present application, the expression "having an insertion, substitution or deletion of one or more amino acids, or addition of such amino acids to either one or both termini" is used to mean that such an insertion, substitution, deletion, or addition of one or more amino acids has been carried out by well-known techniques such as site-directed mutagenesis, or as a result of naturally occurring substitution of plural amino acids.

The modified amino acid sequence of the ADAM11 protein has an insertion, substitution, deletion, or addition to either one or both termini of, for example, 1 to 30, preferably 1 to 20, more preferably 1 to 10, further more preferably 1 to 5, and particularly preferably 1 or 2 amino acids. The modified amino acid sequence can preferably be an amino acid sequence having a conservative substitution of one or more amino acids (preferably one or several, and more preferably 1, 2 or 3 amino acids) with respect to the amino acid sequence of the ADAM11 protein.

The term "conservative substitution" is used herein to mean that one or more amino acid residues are substituted with other chemically similar amino acid residues, so as not to substantially modify the functions of a protein. Examples of such conservative substitution include a case where a certain hydrophobic residue is substituted with another hydrophobic residue and a case where a certain polar residue is substituted with another polar residue having the same electric charge. Such functionally similar amino acids that can be used in such substitution are known as every amino acid types in the present technical field. Specific examples of a nonpolar (hydrophobic) amino acid include alanine, valine, isoleucine, leucine, proline, tryptophan, phenylalanine, and methionine. Examples of a polar (neutral) amino acid include glycine, serine, threonine, tyrosine, glutamine, asparagine, and cysteine. Examples of a (basic) amino acid having a positive charge include arginine, histidine, and lysine. Examples of an (acidic) amino acid having a negative charge include aspartic acid and glutamic acid.

A specific example of a gene (cDNA) that hybridizes with a gene sequence encoding an ADAM11 protein under stringent conditions is a polynucleotide having homology of at least 70%, preferably 80% or more, more preferably 85% or more, further more preferably 90% or more, still further more preferably 95% or more, particularly preferably 98% or more, and most preferably 99% or more, with a nucleotide sequence encoding the ADAM11 protein, when such homology is calculated using default (initialized) parameters according to software used for homology searching, such as FASTA, BLAST, or Smith-Waterman (Meth. Enzym., 164, 765 (1988)). Moreover, the term "under stringent conditions" is used herein to mean that the reaction is carried out in a hybridization buffer that can be generally used by persons skilled in the art, at a temperature between 40° C. and 70° C., and preferably between 60° C. and 65° C., and that the reaction product is then washed in a washing solution having a salt concentration between 15 and 300 mmol/L, and preferably between 15 and 60 mmol/L. The temperature and the salt concentration can be adjusted as appropriate, depending on the length of a probe used. Further, as for the aforementioned washing conditions, the hybridized product may be washed in 0.2 or 2×SSC and 0.1% SDS at a temperature between 20° C. and 68° C. Stringent conditions (high stringency) or mild conditions (low stringency) can be determined by changing a salt concentration or a temperature applied during the washing process. When hybridization conditions are determined using a salt concentration, 0.2×SSC and 0.1% SDS may be used as a stringent wash buffer (high stringency wash buffer), and 2×SSC and 0.1% SDS may be used as a mild wash buffer (low stringency wash buffer). Moreover, when hybridization conditions are determined using a temperature, the reaction may be carried out at 68° C. in the case of stringent conditions, at 42° C. in the case of moderate stringency, and at room temperature (20° C. to 25° C.) in the case of mild conditions, but 0.2×SSC and 0.1% SDS are used in all the cases.

When prehybridization is carried out, in general, it is carried out under the same conditions as those for hybridization. However, the washing process in prehybridization is not necessarily carried out under the same conditions as those for hybridization.

Hybridization can be carried out according to a known method. When a commercially available library is used, hybridization can be carried out according to the method described in instructions included therewith.

In the specification of the present application, the term "identity" (which may also be referred to as "homology") of an amino acid sequence is used to mean the level of concordance of amino acid residues that constitute each sequence. At that time, the presence of gaps and the properties of amino acids are taken into consideration (Wilbur, Proc. Natl. Acad. Sci. U.S.A. 80: 726-730 (1983)). Commercially available software such as BLAST (Altschul: J. Mol. Biol. 215: 403-410 (1990)) or FASTA (Peasron: Methods in Enzymology 183: 63-69 (1990)) can be used in calculating homology.

The amino acid sequence having at least 70% identity with the amino acid sequence of the ADAM11 protein can also be an amino acid sequence having identity of preferably 80% or more, more preferably 85% or more, further more preferably 90% or more, still further more preferably 95% or more, particularly preferably 98% or more, and most preferably 99% or more, with the amino acid sequence of the ADAM11 protein.

All values indicating "identity" may be calculated using a homology searching program known to persons skilled in the art. For example, such values indicating identity may be calculated using default (initialized) parameters in the homologous algorithm "BLAST" program (Basic local alignment search tool) http://www.ncbi.nlm.nih.gov/BLAST/) at the National Center for Biotechnology Information (NCBI).

Disruption of ADAM11 Gene

In the gene-disrupted animal of the present invention, the ADAM11 gene can be disrupted by insertion of a foreign sequence into the ADAM11 gene, by substitution of the entire or a part of the ADAM11 gene with a foreign sequence, or by deletion of the entire or a part of the ADAM11 gene. The number of bases of such a foreign sequence and the position of the ADAM11 gene to be substituted, deleted or inserted are not particularly limited, as long as expression of the ADAM11 protein or the activity thereof is substantially lost. From the viewpoint of selection of a recombinant gene, such a foreign sequence is preferably a selective marker gene. Such a selective marker gene can be appropriately selected from known selective marker genes. Preferred examples of such a selective marker gene include drug resistance genes such as a neomycin resistance gene or a puromycin resistance gene.

The ADAM11 gene can preferably be disrupted by substituting the entire or a part of the ADAM11 gene with a foreign sequence. Examples of a part of the ADAM11 gene to be substituted include an ADAM11 Pro domain and an ADAM11 metalloprotease-like domain. Specifically, a gene region ranging from exon 5 to exon 7 or a gene region ranging from exon 9 to exon 15 can be substituted with a foreign sequence. Moreover, the ADAM11 gene can also be disrupted by introducing a mutation such as a deletion, insertion, or substitution in the above ADAM11 gene. For example, a mutation that has a fatal influence (loss of expression or activity) on the functions of a protein, such as a frameshift mutation or a nonsense mutation, can be introduced into the aforementioned gene.

The technique of disrupting a gene has been known to persons skilled in the art. Such skilled persons are able to disrupt a gene according to known methods. Preferably, the ADAM11 gene can be disrupted by targeted disruption.

Targeted disruption is a technique of introducing nucleic acid obtained by modifying the nucleotide sequence of a gene to be targeted (preferably a selective marker gene, and more preferably a gene into which a drug resistance gene has been inserted) into a cell, causing homologous recombination between the introduced nucleic acid and the target gene, and selecting a homologous recombinant cell, so as to introduce a mutation into the target gene (Capecchi M. R., Science 244: 1288-1292, 1989). Such targeted disruption is an example of the technique of inactivating an ADAM11 gene based on information regarding the nucleotide sequence of the aforementioned gene. Thus, animals with ADAM11 genes that are inactivated by other techniques are also included in the non-human gene-disrupted animal of the present invention.

Nucleic acid used in homologous recombination may be produced by introducing a mutation into the nucleotide sequence of a gene to be targeted by known gene engineering techniques such as chemical synthesis, site-directed mutagenesis, or a PCR method. Moreover, such nucleic acid may also be produced by a positive-negative selection method, which applies homologous recombination (U.S. Pat. Nos. 5,464,764, 5,487,992, and 5,627,059; Proc. Natl. Acad. Sci. USA, Vol. 86, 8932-8935, 1989; and Nature, Vol. 342, 435-438, 1989; etc.).

Gene-disrupted Animal

In the first embodiment of the gene-disrupted animal of the present invention, a non-human gene-disrupted animal produced by disrupting both alleles of an ADAM11 gene and a progeny thereof are provided. In the first embodiment, since the gene-disrupted animal has homozygous disruption of the ADAM11 gene, an ADAM11 protein cannot be expressed. That is to say, according to the first embodiment, a non-human animal whose ADAM11 gene has been knocked-out is provided.

The gene-disrupted animal in the first embodiment has a phenotype that causes a nerve-related disease. Accordingly, a substance used in the treatment of a nerve-related disease can be screened by using the gene-disrupted animal in the first embodiment.

In the present invention, the term "nerve-related disease" is used to have meanings such as incoordination, memory disorder (e.g., spatial or working memory disorder), agnosia, learning disability, and paralgesia.

Incoordination is a disorder caused by the abnormity of a central nervous system such as cerebellum, injury to a peripheral nervous system such as a motor nerve or muscle force, or the abnormity of a skeleton. It becomes impossible to adjust the positions of arms or legs or posture, and thus this disease causes symptoms such as the disappearance of smooth motions or the disappearance of precise motions. In the case of a non-human animal, for example, if this disease is caused by the abnormity of a central nervous system, the disease can be confirmed by a rotor rod test, for example. Moreover, if this disease is caused by the disorder of a peripheral nervous system or muscle force or the abnormity of skeleton, the disease can be confirmed by a grip strength test (tractional force test), a suspension test, a gait test, etc. With regard to these tests, please refer to the method described in Ogura H, Matsumoto M, Mikoshiba K. (2001) Behav Brain Res. 122 (2): 215-219.

Memory disorder, for example, is a disorder caused by injury to hippocampus, and it is attended with symptoms such that a patient suffering from this disease may forget about the promise, may misunderstand the date and the time, or may not understand where he/she is, and thus the patient may not reach his/her destination and may get lost. In the case of a nonhuman animal, for example, the disease can be confirmed by a water maze test.

Paralgesia is a disorder caused by injury to a receptor or an effector mainly relating to pain, or a pathway thereof. This disease brings on symptoms such as the blunting of pain. In the case of a nonhuman animal, for example, the disease can be confirmed by a formalin test or acetic acid rising method.

In the second embodiment of the gene-disrupted animal of the present invention, a non-human gene-disrupted animal produced by disrupting either one allele of an ADAM11 gene and a progeny thereof are provided. Since the gene-disrupted animal in the second embodiment includes heterozygous disruption of the ADAM11 gene, the ADAM11 protein is still expressed. However, as described later, the gene-disrupted animal in the first embodiment including homozygous disruption of the ADAM11 gene can be obtained by crossing a male of the gene-disrupted animals in the second embodiment with a female of the gene-disrupted animals in the second embodiment. That is to say, the gene-disrupted animal in the second embodiment can be used as a parent animal used in production of a non-human gene-disrupted animal in the first embodiment.

The type of a non-human animal is not particularly limited. From the viewpoint of production of an animal model, preferred examples of such a non-human animal are rodents, which can be comparatively easily reproduced and offsprings thereof can be obtained in a comparatively short time. More preferred examples are mice and rats.

The present invention provides a progeny of the non-human gene-disrupted animal of the present invention. The term "progeny" is used in the present invention to mean a progeny having a disrupted ADAM11 gene owned by the gene-disrupted animal of the present invention.

The present invention also provides tissues obtained from the non-human gene-disrupted animal of the present invention or a progeny thereof. Examples of such tissues include all of organs and apparatuses such as brain, heart, thymus gland, kidney, liver, pancreas, muscle, bone, bone marrow, or skin.

The present invention also provides non-human animal cells obtained from the non-human gene-disrupted animal of the present invention or a progeny thereof.

The present invention further provides a breeding material obtained from the non-human gene-disrupted animal of the present invention or a progeny thereof. Examples of such a breeding material include sperm, an unfertilized egg, and a fertilized egg.

Production of Gene-disrupted Animal

The present invention provides a method for producing the non-human gene-disrupted animal in the first embodiment, which comprises the following steps:

transforming non-human animal embryonic stem cells (ES cells) with a polynucleotide containing a disrupted ADAM11 gene;

selecting an ES cell, into the genome of which the above described polynucleotide has been incorporated;

introducing the selected ES cell into a non-human animal embryonic cell;

transplanting the ES cell-introduced non-human animal embryonic cell to the reproductive organ of a wild-type pseudopregnant non-human female animal to reproduce a chimeric animal;

crossing the obtained chimeric animal with a wild-type non-human animal to reproduce a non-human gene-disrupted animal with either one allele of the ADAM11 gene that has been disrupted; and crossing a male of the obtained non-human gene-disrupted animals with a female animal of the obtained non-human gene-disrupted animals to reproduce a non-human gene-disrupted animal with both alleles of the ADAM11 gene that have been disrupted.

The present invention provides a method for producing the non-human gene-disrupted animal in the second embodiment, which comprises the following steps:

transforming non-human animal embryonic stem cells (ES cells) with a polynucleotide containing a disrupted ADAM11 gene;

selecting an ES cell, into the genome of which the above described polynucleotide has been incorporated;

introducing the selected ES cell into a non-human animal embryonic cell;

transplanting the ES cell-introduced non-human animal embryonic cell to the reproductive organ of a wild-type pseudopregnant non-human female animal to reproduce a chimeric animal; and crossing the obtained chimeric animal with a wild-type non-human animal to reproduce a non-human gene-disrupted animal whose either one allele of the ADAM11 gene has been disrupted.

The production of a non-human gene-disrupted mouse of the present invention will be described in detail below. At first, a targeted disruption method applied to an ADAM11 gene will be described in the order of the cloning of the ADAM11 gene, construction of a targeting vector used in targeted disruption, and the obtainment of homologous recombinant ES cells. Production of gene-disrupted animals other than gene-disrupted mice is known in the present technical field. For example, please refer to Dev. Biol. 163(1): 288-292, 1994; Mol. Reprod. Dev. 45(4); 439-443, 1996; Proc. Natl. Acad. Sci. U.S.A. 92(17): 7844-7848, 1995 for information about gene-disrupted rats, gene-disrupted rabbits, and gene-disrupted monkeys, respectively.

Step (a): Transformation of ES Cells

Before production of a polynucleotide that contains a disrupted ADAM11 gene, DNA that contains a part of the ADAM11 gene is prepared.

DNA encoding an ADAM11 protein can be obtained from the genomic DNA or cDNA of a non-human animal by designing primers based on the amino acid sequence as shown in SEQ ID NO:2 and then performing the PCR method, or it can be obtained from the RNA of a non-human animal by performing the RT-PCR method. As another method, such DNA can also be obtained by synthesizing probes based on the nucleotide sequences described in the aforementioned cited documents, selecting clones hybridizing with the aforementioned probes from the genomic DNA library or cDNA library of non-human animals, determining the nucleotide sequences thereof, and selecting a clone containing the nucleotide sequence of the ADAM11 gene or a part thereof, which preferably has a size of 5 kbp or more, and more preferably 10 kbp or more. A restriction site contained in the cloned DNA is confirmed, and a restriction map is then produced. In a case where DNA having a length sufficient for homologous recombination, which is a clone with a size of preferably 5 kbp or more and more preferably 10 kbp or more, cannot be obtained, it is also possible that several clones be cleaved at suitable restriction sites and that the obtained DNA portions be ligated to one another.

A positive selective marker such as drug resistance gene, preferably a neomycin resistance gene or a puromycin resistance gene, is introduced into a restriction site in the exon region of the thus obtained DNA having a length sufficient for homologous recombination. Moreover, it may also be possible that a portion of the exon be eliminated and that the portion be substituted with a drug resistance gene.

When no suitable restriction sites are found, it may also be possible that the PCR method be performed and that a suitable restriction site be introduced by ligation of an oligonucleotide including a restriction site, etc. Preferably, in order to eliminate embryonic stem cells (ES cells) obtained due to the fact that homologous recombination has not occurred between the introduced DNA and the ADAM11 gene and thus that the introduced DNA has been inserted into sites other than the ADAM 11 gene, a vector may preferably include a negative selective marker such as a thymidine kinase gene or a diphtheria toxin gene. Such recombinant DNA techniques of manipulating the nucleotide sequences of such DNA can be carried out by the method described in Sambruck, J., Fritsch, E. F., and Maniatis, T. (1989) Molecular Cloning: A Laboratory Manual, Cold Spring Harbor Laboratory, Cold Spring Harbor, N.Y. If suitable recombinant DNA can be obtained, methods to be applied are not limited to the aforementioned methods. The type of a vector used in production of a targeting vector is not particularly limited. Any type of vector can be used, as long as it can autonomously replicate in cells to be transformed (e.g., *Escherichia coli*). For example, commercially available pBluescript (Stratagene), pZErO1.1 (Invitrogen), pGEM-1 (Promega), etc. can be used.

Step (b): Selection of Transformed ES Cells

The produced targeting vector is cleaved with restriction enzymes to form linear DNA. The thus obtained DNA is then purified by phenol-chloroform extraction, agarose electrophoresis, ultracentrifugation, etc. Thereafter, ES cells such as TT2 are transfected with such purified DNA. Transfection methods include electroporation and lipofectin, but methods are not limited thereto in the present invention. The transfected ES cells are cultured in a suitable selective medium. In a case where a targeting vector into which a neomycin resistance gene and a thymidine kinase gene have been incorporated is produced, for example, the ES cells are cultured in a selective medium containing neomycin and ganciclovir. Incorporation of the introduced gene such as a neomycin resistance gene into the grown ES cells, which have exhibited drug resistance to both the drugs, can be easily identified by the PCR method or the like. Moreover, whether or not homologous recombination has occurred can also be confirmed by performing Southern blot analysis using, as a probe, a portion of DNA located upstream of the 5'-terminus or downstream of the 3'-terminus outside of the targeting vector. Furthermore, Southern blot analysis is carried out using DNA contained in the targeting vector as a probe, so as to confirm that the targeting vector has not been randomly inserted. These methods are used in combination, so as to obtain homologous recombinant ES cells.

Step (c): Introduction of ES Cells into Embryo or Blastocyst

An ADAM11 gene knockout mouse can be produced by such steps as collection of an 8-cell-stage embryo or blastocyst after fertilization, microinjection of homologous recombinant ES cells, transplantation of a manipulated egg into a pseudopregnant mouse, the delivery of the pseudopregnant mouse and breeding of born babies, selection of the gene-introduced mouse by the PCR method and the Southern blotting method, and the establishment of a mouse line having the introduced gene (Yagi, T. et. al., Analytical Biochem. 214, 70, 1993).

ES cells can also be introduced into an embryo or blastocyst by the following.

With regard to collection of a fertilized egg such as an 8-cell-stage embryo or blastocyte, in order to induce superovulation of a female mouse, at first, 5 international units of pregnant mare's serum gonadotrophin and 2.5 international units of human chorionic gonadotropin were intraperitoneally administered to the female mouse. Thereafter, 2.5 days after fertilization, an 8-cell-stage embryo is obtained from the female mouse by an oviduct-uterus reflux method. When a blastocyte is used, 3.5 days after fertilization, uterus is extracted from the female mouse, and an embryo is then obtained by uterus reflux.

Subsequently, homologous recombinant ES cells were injected into the obtained 8-cell-stage embryo or blastocyte by microinjection. Microinjection can be carried out using a micromanipulator, a microinjector, an injection pipette, and a holding pipette, under an inverted microscope, based on the descriptions of Hogan, B. L. M., A laboratory Manual, Cold Spring Harbor Laboratory Press, Cold Spring Harbor, N.Y., 1986; and Yagi T. et al., Analytical Biochem. 214, 70, 1993, for example. In addition, as an injection dish, droplets are produced by suspending 5 µl of medium droplets and ES cells in Falcon 3002 (Becton Dickinson Labware), and liquid paraffin is laminated onto the produced droplets. Hereinafter, an 8-cell-stage embryo or blastocyte, into which homologous recombinant ES cells have been microinjected, is referred to as a manipulated egg.

Steps (d) and (e): Transplantation of Manipulated Egg into Pseudopregnant Mouse and Establishment of Heterozygous Mouse A vasoligated male mouse was crossed with a normal female mouse to produce a pseudopregnant mouse. A manipulated egg is then transplanted into the pseudopregnant mouse. Transplantation of such a manipulated egg is carried out, based on the descriptions of Hogan, B. L. M., A Laboratory Manual, Cold Spring Harbor Laboratory Press, Cold Spring Harbor, N.Y., 1986, or Yagi T. et. al., Analytical Biochem. 214, 70, 1993. Examples of specific operations will be described below, but the present invention is not limited thereto.

A pseudopregnant mouse is subjected to general anesthesia using 50 mg/kg (body weight) of pentobarbital sodium. Thereafter, both tendon portions are excised at a size of approximately 1 cm, so that an ovary and an oviduct are exposed. Thereafter, bursa ovarica is excised with tweezers under a stereoscopic microscope, and imbriae of uterine tube is exposed. Subsequently, 7 or 8 manipulated eggs per oviduct are sent into the imbriae of uterine tube. At the time, microbubbles sent together with the manipulated eggs are used to confirm transplantation of the manipulated eggs into the oviduct. Thereafter, the oviduct and the ovary are returned to the abdominal cavity, and the excised portions are then sutured. Thereafter, the mouse is awoken. In some cases, such a manipulated egg may be cultured until the next day, so that it is allowed to grow up to a blastocyte, and the blastocyte may be then transplanted into the uterus.

In many cases, baby mice can be obtained on the 17th day after such transplantation. Such baby mice are generally chimeric mice having homologous recombinant ES cells and the cells of a mouse, from which a fertilized egg has been collected. When TT2 is used as such ES cells and it is injected into an 8-cell-stage embryo collected from an ICR mouse, for example, baby mice with a high chimeric rate predominantly have a wild mouse hair color, whereas the hair color of baby mice having a low chimeric rate is predominantly white.

Whether or not the introduced gene has been incorporated into germ cells can be easily confirmed by crossing a mouse to be examined with a mouse with white hair (e.g., ICR) and observing the hair color of the obtained baby mice. Since it is anticipated that a mouse having a high chimeric rate contains the introduced gene in the germ cells thereof, it is preferable to select a mouse having a chimeric rate that is as high as possible.

The obtained chimeric mouse is crossed with a wild-type mouse (normal mouse), so as to obtain a heterozygous mouse (hereinafter referred to as a "hetero mouse" at times). DNA is extracted from the tail of the obtained baby mouse, and the presence or absence of the introduced gene can be then confirmed by the PCR method. In addition, instead of the PCR method, the Southern blot analysis can be applied to more reliably identify a genotype.

Step (f): Establishment of Homozygous Mouse Line

When the two heterozygous mice are crossed to obtain baby mice, ADAM11 gene knockout mice (hereinafter referred to as "homo mice"), wherein the introduced gene exists in a homozygous manner, can be obtained. Such an ADAM11 knockout mouse can be obtained by any one of the crossing of the two heterozygous mice, the crossing of the heterozygous mouse with the ADAM11 gene knockout mouse, and the crossing of the two ADAM11 gene knockout mice. The presence or absence of expression of the mRNA of such an ADAM11 gene knockout mouse can be confirmed by the Northern blot analysis, the RT-PCR method, the RNAse protection assay, the in situ analysis, etc. Moreover, expression of an ADAM11 protein can be confirmed by immunohistological staining, the use of an antibody that recognizes the aforementioned protein, etc.

Screening Method

The non-human gene-disrupted animal in the first embodiment of the present invention has a phenotype of nerve-related disease such as incoordination, memory disorder (e.g., spatial or working memory disorder), agnosia, learning disability, or paralgesia. Since the non-human gene-disrupted animal in the first embodiment has a homozygous disruption of the ADAM11 gene, it is considered that a phenotype of nerve-related disease is caused by inactivation of the ADAM11 gene. Accordingly, the non-human gene-disrupted animal in the first embodiment of the present invention can be used as a model animal of a nerve-related disease caused by inactivation of the ADAM11 gene. In particular, the above non-human gene-disrupted animal can be used in the searching and development of a therapeutic agent for central nervous system disease or paralgesia, or in the function analysis of a central nervous system such as learning, memory, motor function or somatic sense, or a pain pathway (in particular, function analysis at a molecular level).

The present invention provides a method for screening for a substance used in the treatment of a nerve-related disease, a salt thereof, or a solvate thereof, which comprises the following steps:
  (i) measuring the severity of a symptom of the nerve-related disease of the non-human gene-disrupted animal in the first embodiment;
  (ii) administering a test substance to the above described non-human gene-disrupted animal; and
  (iii) measuring the severity of a symptom of the nerve-related disease of the above described non-human gene-disrupted animal after administration of the test substance.

The screening method of the present invention may further comprise the following step after step (iii):
  (iv) comparing the severity of a symptom of the nerve-related disease before administration of the test substance with the severity of a symptom of the nerve-related disease after administration of the test substance.

The type of a substance screened by the screening method of the present invention is not particularly limited. Examples of such a substance include a therapeutic agent for treating a nerve-related disease or a candidate compound therefor. Specific examples of such a substance used as a screening target include an ataxia-improving agent, a memory-improving agent, an analgesia-improving agent, and a candidate compound therefor.

Such a substance screened by the screening method of the present invention may be either a salt or a solvate. Examples of a salt with acid include: inorganic acid salts such as hydrochloride, hydrobromide, sulfate, or phosphate; and salts with organic acids such as formic acid, acetic acid, lactic acid, succinic acid, fumaric acid, maleic acid, citric acid, tartaric acid, benzoic acid, methanesulfonic acid, benzenesulfonic acid, p-toluenesulfonic acid, or trifluoroacetic acid. Examples of a salt with a base include: alkaline metal salts such as a sodium salt or a potassium salt; alkaline-earth metal salts such as a calcium salt or a magnesium salt; salts with organic bases (organic amine salts) such as trimethylamine, triethylamine, pyridine, picoline, dicyclohexylamine, N,N'-dibenzylethylenediamine, arginine, or lysine; and ammonium salts.

Moreover, such a substance screened by the screening method of the present invention may be an anhydride, or may form a solvate such as a hydrate. Such a solvate may be either a hydrate or a non-hydrate, but a hydrate is preferable. Examples of a solvent used herein include water, alcohol (methanol, ethanol, or n-propanol, for example), and dimethylformamide. When a solvate thereof and/or an optical isomer thereof are present, such a solvate and/or an optical isomer are included in the substance screened by the screening method of the present invention.

Furthermore, the substance screened by the screening method of the present invention also includes a substance, which is subjected to metabolism such as oxidation, reduction, hydrolysis, or conjugation in a living body.

Still further, the substance screened by the screening method of the present invention also includes a compound, which is subjected to metabolism such as oxidation, reduction, or hydrolysis in a living body, and generates a sulfonamide compound.

In the screening method of the present invention, the severity of a symptom of the nerve-related disease of a gene-disrupted animal before administration of a test substance are compared with the severity of a symptom of the nerve-related disease of the gene-disrupted animal after administration of the test substance. When the latter levels are improved rather than the former levels, it can be determined that the test substance is useful for the treatment of the nerve-related disease. A rotor rod test, a water maze test, a formalin test, an acetic acid rising test, etc. can be used to measure the levels of the symptoms.

A rotor rod test is used to examine the disorder of motor coordination. An animal is placed on a rotating rod (which preferably rotates at 1 to 20 times for 1 minute), and a falling frequency or a time required until the animal falls is then examined. In the screening method of the present invention, the non-human gene-disrupted animal of the present invention is placed on a rotating rod before administration of a test substance, and a falling frequency or a time required until the animal falls is then measured. Subsequently, the non-human gene-disrupted animal in the first embodiment is placed on a rotating rod after administration of the test substance, and a falling frequency or a time required until the animal falls is then measured. When such a falling frequency is decreased or the time required until the animal falls is prolonged after administration of the test substance, it can be determined that the aforementioned test substance is a substance for improving motor coordination functions.

In a water maze test, for example, a pool with a diameter between 1 and 2 m is filled with water that has become clouded with milk, ink, or the like, as necessary, and a platform for evacuation is then established at a certain place in the pool. The non-human gene-disrupted animal in the first embodiment is allowed to swim in the pool. Thereafter, the time (escape latency) required until the animal reaches the platform (finish line) where the animal is able to keep its feet on the ground is measured. The result can be used as an indicator of spatial cognitive ability. In the screening method of the present invention, the non-human gene-disrupted animal of the present invention is subjected to such a water maze test before administration of a test substance, and the time required until the animal reaches the platform is measured. Subsequently, the test substance is administered to the animal, and the water maze test is carried out again. Thus, the time required until the animal reaches the platform is measured again. If the time required until the animal reaches the platform after administration of the test substance is shorter than the time required until the animal reaches the platform before administration of the test substance, it can be determined that the aforementioned test substance is a substance for improving memory disorder (including cognitive disorder, learning disorder, etc.).

A formalin test is used to observe and evaluate the pain of an animal. This test relates to a clear behavior for expressing pain (for example, shaking, licking, or biting a leg, into which something has been injected). In the screening method of the present invention, for example, the state of a leg of the non-human gene-disrupted animal of the present invention is observed before administration of formalin thereto. Thereafter, a test substance is administered to the leg of the aforementioned animal, and the state of the leg is observed (licking or biting). If the animal reacts to its leg more quickly after administration of the test substance than before administration of the test substance, it can be determined that the aforementioned test substance is a substance for improving paralgesia.

With regard to an acetic acid rising test, if acetic acid is administered to a mouse, the mouse has a unique "symptom of writhing (rising)" due to pain. In the screening method of the present invention, for example, the state of the non-human gene-disrupted animal of the present invention is observed before intraperitoneal administration of acetic acid. Subsequently, a test substance is intraperitoneally administered to the aforementioned animal, and the state of the animal (rising, etc.) is then observed. If the rising state occurs more quickly after administration of the test substance than before administration of the test substance, it can be determined that the aforementioned test substance is a substance for improving paralgesia.

Pharmaceutical Composition and Gene Therapy Agent

The present invention provides a pharmaceutical composition for use in the treatment of a nerve-related disease caused by inactivation of an ADAM11 gene, which comprises an ADAM11 protein.

The present invention also provides use of an ADAM11 protein for the manufacture of a medicament used in the treatment of a nerve-related disease caused by inactivation of an ADAM11 gene.

The present invention further provides a method for treating a nerve-related disease caused by inactivation of an ADAM11 gene, which comprises the step of administering to a patient in need thereof, a therapeutically effective amount of the ADAM11 protein.

The term "treatment" is used in the present specification to generally mean that a desired pharmacological effect and/or physiological effect can be obtained. Such an effect is preventive from the viewpoint of a complete or partial prevention of diseases and/or symptoms, but it is therapeutic from the viewpoint of a partial or complete treatment of adverse effects caused by diseases and/or symptoms. The term "treatment" is used in the present specification to include any given treatment of the diseases of mammals, and in particular, of humans. The term "treatment" includes the following treatments, for example:

prevention of the development of a disease or a symptom from a patient who may have a predisposition of the disease or the symptom but has yet been diagnosed to have the disease or the symptom;

inhibition of the symptoms of a disease, namely, inhibition or retardation of the progression thereof; and alleviation of the symptoms of a disease, namely, regression of the disease or the symptoms, or inversion of the progression of the symptoms.

In the present specification, examples of the "nerve-related disease caused by inactivation of an ADAM11 gene" include incoordination, memory disorder (e.g., spatial or working memory disorder), agnosia, learning disability, and paralgesia.

In the treatment using an ADAM11 protein, such an ADAM11 protein is mixed with a pharmaceutically acceptable carrier, so that it can be provided in the form of a pharmaceutical composition.

The ratio of an active ingredient to a carrier can be changed between 1% and 90% by weight. In addition, the pharmaceutical composition of the present invention can be administered to humans or organisms other than the humans [for example, non-human mammals (e.g., a bovine, a monkey, a cat, a mouse, a rat, a hamster, a swine, a canine, etc.), birds, reptiles, amphibians, fish, insects, etc.] in various forms via either an oral administration route or a parenteral administration route (e.g., intravenous injection, intramuscular injection, subcutaneous administration, rectal administration, and dermal administration). That is to say, the pharmaceutical composition of the present invention can be administered to humans or organisms other than the humans in various forms via either an oral administration route or a parenteral administration route (e.g., intravenous injection, intramuscular injection, subcutaneous administration, rectal administration, and dermal administration). Accordingly, as the pharmaceutical composition of the present invention, an active ingredient can be used singly. However, it is also possible to formulate such an active ingredient with a pharmaceutically acceptable carrier by a method commonly used depending on an administration route, so as to manufacture a formulation having a suitable dosage form.

Examples of a preferred dosage form include: oral agents such as a tablet, a powder, a parvule, a granule, a coated tablet, a capsule, a syrup, or a troche; and a parenteral agents such as an inhalant, a suppository, an injection (including drops), an ointment, eye drops, an eye ointment, nasal drops, ear drops, a cataplasm, a lotion, or a ribosomal agent.

Examples of a carrier used to manufacture such formulations include: a commonly used excipient, binder, disintegrator, lubricant, coloring agent, and flavoring agent; and, as necessary, a stabilizer, an emulsifier, an absorption promoter, a surfactant, a pH adjuster, an antiseptic, an antioxidant, an extender, a moistening agent, a surface activator, a dispersant, a buffer, a preservative, a solubilizer, and a soothing agent. Components that are generally used as materials for pharmaceutical preparations are mixed according to common methods, so as to manufacture formulations. Examples of such usable nontoxic components include: animal and plant oils such as soybean oil, beef tallow, or synthetic glyceride; hydrocarbons such as liquid paraffin, squalane, or solid paraffin; ester oils such as octyldodecyl myristate or isopropyl myristate; higher alcohols such as cetostearyl alcohol or behenyl alcohol; silicon resins; silicon oils; surfactants such as a polyoxyethylene fatty acid ester, a sorbitan fatty acid ester, a glycerine fatty acid ester, a polyoxyethylene sorbitan fatty acid ester, polyoxyethylene hydrogenated castor oil, or a polyoxyethylene-polyoxypropylene block copolymer; water-soluble polymers such as hydroxyethyl cellulose, polyacrylic acid, a carboxyvinyl polymer, polyethylene glycol, polyvinylpyrrolidone, or methyl cellulose; lower alcohols such as ethanol or isopropanol; polyalcohols (polyols) such as glycerin, propylene glycol, dipropylene glycol, sorbitol, or polyethylene glycol; sugars such as glucose or sucrose; inorganic powders such as silicic acid anhydride, magnesium aluminum silicate, or aluminum silicate; inorganic salts such as sodium chloride or sodium phosphate; and purified water.

Examples of an excipient include lactose, fructose, corn starch, saccharose, glucose, mannitol, sorbit, crystalline cellulose, and silicon dioxide. Examples of a binder include polyvinyl alcohol, polyvinyl ether, methylcellulose, ethylcellulose, gum Arabic, Tragacanth, gelatin, shellac, hydroxypropylmethylcellulose, hydroxypropylcellulose, polyvinylpyrrolidone, a polypropylene glycol-polyoxyethylene block polymer, and meglumine. Examples of a disintegrator include starch, agar, gelatin powders, crystalline cellulose, calcium carbonate, sodium bicarbonate, calcium citrate, dextrin, pectin, and carboxymethylcellulose calcium. Examples of a lubricant include magnesium stearate, talc, polyethylene glycol, silica, and hydrogenated vegetable oil. Examples of a coloring agent include those allowed to be added to pharmaceuticals. Examples of a flavoring agent include cocoa powders, menthol, aromatic powder, peppermint oil, borneol, and cinnamon powders. The aforementioned components may also include the salts thereof and the solvates thereof.

For production of oral agents, an excipient, and as necessary, a binder, a disintegrator, a lubricant, a coloring agent, a flavoring agent, etc. are added to the active ingredient used in the present invention, and the mixture is then processed according to a common method, so as to produce a powder, a parvule, a granule, a tablet, a coated tablet, a capsule, etc. In the case of a tablet and a granule, it is naturally possible to coat them with glycocalyo or other coating agents, as appropriate. In the case of a syrup, an injection, and the like, a pH adjuster, a resolvent, an isotonizing agent, etc. and as necessary, a solubilizer, a stabilizer, etc. are added to the active ingredient used in the present invention, and the mixture is then processed according to a common method, so as to produce a formulation. In addition, in the case of an external preparation, a production method thereof is not particularly limited, and such an external preparation can be produced by a common method. As usable base materials, various types of materials, which are generally used for pharmaceuticals, quasi drugs, cosmetic products, etc., can be used. Examples of such a material include animal and plant oil, mineral oil, ester oil, waxes, higher alcohols, fatty acids, silicon oil, a surfactant, phospholipids, alcohols, polyalcohols, water-soluble polymers, clay minerals, and purified water. To such materials, a pH adjuster, an antioxidant, a chelating agent, an antiseptic and antifungal agent, a coloring agent, an aromatic, etc. may be added, as necessary. Furthermore, components such as a blood flow promoter, a germicide, an antiphlogistic, a cell activator, vitamins, amino acid, a moisturizer, or a keratolytic drug may be mixed into the aforementioned active ingredient, as necessary. At the time, the ratio of the active ingredient to the carrier can be changed between 1% and 90% by weight. The active ingredient contained in the pharmaceutical composition of the present invention is preferably purified at a level of at least 90%, preferably 95% or more, more preferably 98% or more, and further more preferably 99% or more, before use.

The administration form and necessary dosage range of the pharmaceutical composition of the present invention depend on a target to which the pharmaceutical composition is to be administered, an administration route, the properties of the pharmaceutical composition, the condition of a patient, and the judgment of a doctor. However, a suitable dosage is, for example, approximately 0.1 to 500 µg, preferably approximately 0.1 to 100 µg, and more preferably approximately 1 to 50 µg, per kg of body weight of a patient. Taking into consideration the fact that efficiency is different depending on an administration route, it is anticipated that a necessary dosage fluctuates in a wide range. For example, it is anticipated that a higher dosage is required in oral administration than in intravenous injection. Such fluctuation of a dosage level can be adjusted by standard empirical optimizing procedures, which are well understood in the present technical field.

The pharmaceutical composition of the present invention and the active ingredient of the gene therapy agent as described later may include a prodrug thereof. A pharmaceutical composition can be produced from a substance discovered by the screening method of the present invention according to the above descriptions.

The term "prodrug" is used in the present specification to mean an agent, which is obtained by chemical modification of a "active moiety of the agent," (which means an "agent" that corresponds to the prodrug) for the purpose of the improvement of bioavailability, alleviation of side effects, etc., and which is then metabolized to a main active body in a body after it has been absorbed and which then exerts its action. Accordingly, the term "prodrug" is used to mean any given compound, peptide, or polynucleotide, which has intrinsic activity lower than that of the corresponding "agent," but when it is administered to a biological system, it generates a substance that acts as an "agent," as a result of a spontaneous chemical reaction, enzyme reaction, or metabolic reaction. Examples of such a prodrug include various types of prodrugs, such as compounds, peptides, or polynucleotides, which are obtained by acylation, alkylation, phosphorylation, boration, carbonation, esterification, amidation, or urethanation of an amino group, a hydroxyl group, a carboxyl group, etc. of the aforementioned compounds, peptides, or polynucleotides. However, the exemplified groups are not comprehensive, but only typical examples. Persons skilled in the art are able to prepare various types of known prodrugs from the aforementioned compounds, peptides, or polynucleotides according to known methods. Such prodrugs prepared from the aforementioned compounds, peptides, or polynucleotides are included in the scope of the present invention.

The present invention provides a gene therapy agent for treating a nerve-related disease caused by inactivation of an ADAM11 gene, which contains a gene transfer vector to which the ADAM11 gene is operably linked.

The present invention also provides use of a gene transfer vector to which an ADAM11 gene is operably linked for the manufacture of a gene therapy agent for use in the treatment of a nerve-related disease caused by inactivation of the ADAM11 gene.

The present invention further provides a method for treating a nerve-related disease caused by inactivation of an ADAM11 gene, which comprises the step of administering to a mammal, the ADAM11 gene or a gene transfer vector to which the ADAM11 gene is operably linked.

In the gene therapy of the present invention, it may be possible to select either an "in vivo method" of directly administering a gene-introduced vector to a patient, or an "ex vivo method" of collecting a target cell from a patient body, introducing an ADAM11 gene or a gene-introduced vector into the target cell outside of the body, and returning the target cell, into which the aforementioned gene or vector has been introduced, to the patient body.

In the case of the in vivo method, the gene-introduced vector is directly administered to a patient by using a gene-introduced vector known in the present technical field, such as a retrovirus vector. As with the pharmaceutical composition of the present invention, such an ADAM11 gene used in the gene therapy of the present invention, or a gene transfer vector to which the ADAM11 gene is operably linked, can be mixed with a pharmaceutically acceptable carrier, so as to produce a formulation. Such a formulation can be parenterally administered, for example. Fluctuation of a dosage level can be adjusted by standard empirical optimizing procedures, which are well understood in the present technical field. In the in vivo method, an ADAM11 gene or a gene transfer vector to which the ADAM11 gene is operably linked, can be administered using a catheter or a gene gun according to a common method.

In the case of the ex vivo method, such an ADAM11 gene can be introduced into a target cell according to a method known in the present technical field, such as the calcium phosphate method, the electroporation method, or the viral transduction method. Such a target cell can be collected from the affected region of a cerebral nerve system or the like. In the case of selecting the ex vivo method, an ADAM11 gene or a gene transfer vector to which the ADAM11 gene is operably linked is introduced into a cell, and the aforementioned peptide is then allowed to express in the cell. Thereafter, the cell is transplanted to a patient, so that a nerve-related disease caused by inactivation of the ADAM11 gene can be treated.

A gene-introduced vector available for gene therapy is well known in the present technical field, and it can be selected, as appropriate, depending on a gene introduction method or a host. Examples of such a vector include an adenovirus vector and a retrovirus vector. When an ADAM11 gene is ligated to a gene-introduced vector, a control sequence such as a promoter or a terminator, a signal sequence, a polypeptide-stabilizing sequence, etc. may be appropriately ligated, such that the gene can be expressed in a host. For selection or construction of such a gene-introduced vector, please refer to the following publications, for example: Miller, A. D., Blood, 76, 271-278, 1990, Vile, R. G., Gene Therapy, Churchill Livingstone, 12-30, 1995, Emi, N., et al., J. Virol., 65, 120 2-1207, 1991, Yee, J. K., et al., Proc. Natl. Acad. Sci. USA, 91, 9564-9568, 1994, Yang, Y., et al. Hum. Gene. Ther. 6, 1203-1213, 1995 Chen, S. T., et al. Proc. Natl. Acad. Sci. USA, 93, 10057-10062, 1996, Ory, D. S. et al., Proc. Natl. Acad. Sci. USA, 93, 11400-11406, 1996, etc.

The present invention provides a cell used in the gene therapy of a nerve-related disease, which is obtained by introducing an ADAM11 gene or a gene transfer vector to which the ADAM11 gene is operably linked, into a cell collected from a living body.

EXAMPLES

The present invention will be described in detail in the following examples. However, these examples are not intended to limit the scope of the present invention.

Example 1

Production of ADAM11 Gene Knockout Mouse 1.1.1: Cloning of ADAM11 Gene

The amino acid sequence of a mouse ADAM11 gene is reported in Gene, 236: 79-86. (1999) and the cDNA sequence is registered with GenBank under Accession Number AB009676. A homologous sequence used in targeting was acquired by amplifying exon 5 and a sequence portion of approximately 3.8 kbp upstream thereof, and exon 7 and a mouse genome sequence of 6.3 kbp downstream thereof, by the PCR method. Specifically, primers (SEQ ID NO:5, SGN055N; and SEQ ID NO:6, SGN043S) were designed, and the PCR method was carried out using the genomic DNA of a C57BL/6 mouse as a template, so as to amplify an approximately 5-kbp DNA fragment. Thereafter, the DNA fragment was digested with HindIII and SalI, so as to obtain an approximately 3.8-kbp fragment (SEQ ID NO:7). Likewise, primers (SEQ ID NO:8, SGN034S; and SEQ ID NO:9, SGN037S) were used, and the PCR method was carried out using the genomic DNA of a C57BL/6 mouse as a template, so as to obtain an approximately 6.3-kbp DNA fragment (SEQ ID NO:10).

1.1.2: Construction of Targeting Vector (pKO-MDC9)

A targeting vector was constructed by the following method. First, a 5'-arm (the fragment as shown in SEQ ID NO:7), a neomycin resistance gene (PGK-neo), and a 3'-arm (the fragment as shown in SEQ ID NO:10) were successively ligated to one another according to a common method. The thus obtained product was then introduced into a pUC18 vector that contained a herpes simplex virus thymidine kinase gene used as a negative selective gene, so as to produce a targeting vector (pKO-MDC9) (FIG. 1).

1.1.3: Obtainment of Homologous Recombinant Embryonic Stem Cells (ES Cells)

The targeting vector pKO-MDC9 was cleaved with NotI to obtain linear DNA (1 mg/ml). TT2 (Gibco BRL, Tokyo) was used as mouse embryonic stem cells (ES cells) (Yagi T. et al., Analytical Biochem. 214, 70, 1993). ES cells ($1 \times 10^7$ cells/ml) were transfected with a linear target vector (200 μg/ml) via electroporation (250 V, 975 μF, room temperature). From two days after the culture, the cells were cultured in a medium that contained G418 (250 μg/ml) and Ganciclovir (0.2 μM) for 3 days. Thereafter, they were further cultured in a medium that contained G418 for 3 days. DNA was extracted from strains randomly selected from among the generated ES cell colonies. Using a nucleotide sequence (SEQ ID NO:11, SGN033) outside of the targeting vector and a nucleotide sequence (SEQ ID NO:12, AGN1) contained in the introduced gene (neomycin resistance gene) as primers, PCR was carried out. Clones that generated an approximately 6.5-kb PCR product were defined as candidates that were likely to involve homologous recombination.

A clone, which involved only homologous recombination, was identified from among such candidate clones by the Southern blot analysis. The extracted genome was cleaved with BamHI, and it was then allowed to hybridize with a BE2K probe (an approximately 2.0-kbp DNA fragment located upstream of the 5'-arm of the targeting vector; SEQ ID NO: 13; refer to FIG. 1). As a result, a wild-type clone was detected in the form of a 13.7-kb band, whereas a homologous recombinant clone was detected in the form of a 10.3-kb band. Thus, the latter clone was selected as a homologous recombinant clone (FIG. 2).

1.1.4: Production of ADAM11 Gene Knockout Mouse 5 international units of pregnant mare's serum gonadotrophin (PMSG; Serotropin; Teikoku Hormone Mfg. Co., Ltd., Tokyo) and 2.5 international units of human chorionic gonadotropin (hCG; Gonatropin; Teikoku Hormone Mfg. Co., Ltd., Tokyo) were intraperitoneally administered to a female mouse (ICR; Charles River Laboratories Japan, Inc.; Kanagawa). On the $2.5^{th}$ day after fertilization, an 8-cell-stage embryo was obtained by an oviduct-uterus reflux method.

The homologous recombinant ES cells were injected into the obtained 8-cell-stage embryo by microinjection. Microinjection was carried out under an inverted microscope (Diaphoto TMD; Nikon, Tokyo), using a micromanipulator (wherein a suspension joystick three-dimensional hydraulic micromanipulator was mounted on a coarse motion electric manipulator; Narishige, Tokyo), a microinjector (Narishige, Tokyo), an injection pipette, and a holding pipette. As an injection dish, droplets were produced by suspending 5 μl of medium droplets and ES cells in Falcon 3002 (Becton Dickinson Labware) and laminating liquid paraffin to the produced droplets.

A vasoligated male mouse (ICR; Charles River Laboratories Japan, Inc.; Kanagawa) was crossed with a normal female mouse (ICR; Charles River Laboratories Japan, Inc.; Kanagawa) to produce a pseudopregnant mouse. A manipulated egg, into which 3 different homologous recombinant ES cell clones had been injected via microinjection, was transplanted into the pseudopregnant mouse. Thereafter, the pseudopregnant mouse was subjected to general anesthesia using 50 mg/kg (body weight) of pentobarbital sodium (Nembutal; Abbott Laboratories). Both tendon portions were excised at a size of approximately 1 cm, so that an ovary and an oviduct were exposed. Thereafter, bursa ovarica was excised with tweezers under a stereoscopic microscope, and imbriae of uterine tube was exposed. Subsequently, 7 or 8 manipulated eggs per oviduct were sent into the imbriae of uterine tube. Thereafter, the oviduct and the ovary were returned to an abdominal cavity, and the excised portions were then sutured.

From the pregnant mouse, into which such manipulated eggs had been transplanted, 100% chimeric mice having a wild mouse hair color were obtained. In order to confirm that the germ cells of the obtained 100% chimeric mice were derived from ES cells, the mice were crossed with ICR female mice, and the obtain baby mice were checked. As a result, it was confirmed that all the baby mice had a wild mouse hair color, and that the germ cells of the chimeric mice were derived from ES cells. Such a chimeric mouse was crossed with a C57BL/6 mouse to obtain a hetero mouse. Thereafter, such two hetero mice were crossed to obtain an ADAM11 gene knockout mouse.

1.2.1: Analysis of ADAM11 Gene Disruption (Southern Blot Analysis)

The genotypes of six male mice with an age of 6 months old (individual numbers 1, 2, 3, 4, 5, and 6) obtained by crossing two hetero mice were confirmed by Southern blot analysis. 20 μg of genomic DNA extracted from the liver of each mouse was cleaved with BamHI, and it was then separated by 7.5% agarose electrophoresis. Thereafter, the separated product was transcribed onto a nylon membrane, and it was then allowed to hybridize with an isotope-labeled BE2K probe. After the membrane had been washed, the image of the hybridized labeled probe was analyzed with a BAS5000 bio-image analyzer (FUJI FILM).

Figure 3:
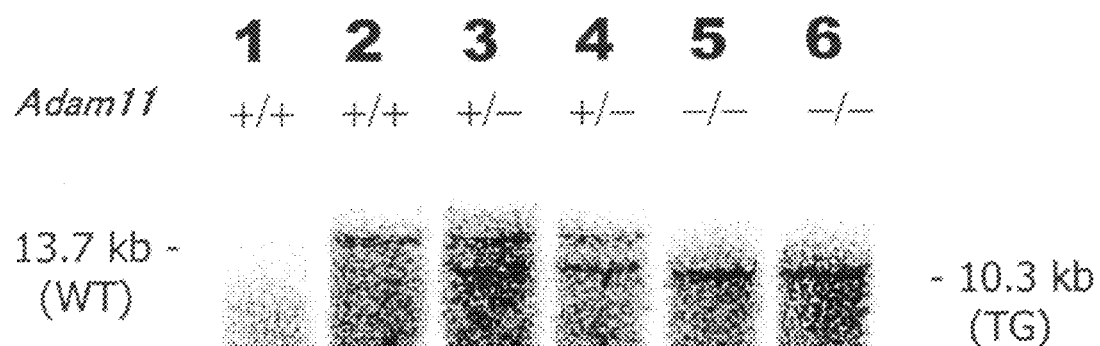
FIG. 3 shows the Southern blot analysis using the genomic DNA of a mouse with a disrupted ADAM11 gene.

As a result, only a 10.3-kb band was detected in the genomic DNA derived from individual numbers 5 and 6. Accordingly, it was confirmed that the mice with individual numbers 5 and 6 were ADAM11 gene knockout mice having both alleles that had been disrupted (FIG. 3).

1.2.2: Analysis of ADAM11 Gene Disruption (Western Blot Analysis)

A cerebellum was excised from each of the six mice used in the analysis described in section 1.2.1, and it was then immersed in 1 ml of a TN(+) solution (50 mM Tris-HCl, ph 7.5, 150 mM NaCl, 1% NP-40, 1×Complete™), followed by disintegration with a polytron homogenizer, so as to produce a cerebellum lysate. Thereafter, 100 μl of Concanavalin A-Sepharose (Amersham) was added to the cerebellum lysate, and the obtained mixture was then cultured at a room temperature for 60 minutes. Subsequently, Concanavalin A-Sepharose was washed twice with a TN(+) solution, and it was then suspended in 120 μl of SDS-PAGE sample loading solution, and an elution operation was then carried out at 95° C. for 3 minutes, so as to produce a concentrated glycoprotein sample derived from the mouse cerebellum that had bound to Concanavalin A. The aforementioned sample was separated by 10% SDS-PAGE, and it was then transcribed onto a PVDF membrane. The transcribed PVDF membrane was blocked in a Block Ace solution (Dainippon Pharma Co., Ltd.) at a room temperature for 1 hour, and it was then treated with a 1 μg/ml anti-ADAM11 monoclonal antibody (Japanese Patent Laid-Open Publication No. 330799/1995) at a room temperature for 3 hours. The PVDF membrane was washed three times, and it was then treated with an anti-mouse IgG-HRP conjugate (Amersham) at a room temperature for 1 hour. The resultant was washed three times, and thereafter, using an ECL-Plus reagent (Amersham), an ADAM11 protein was detected. At the same time, a HeLa cell lysate, wherein an HA tag-added mouse ADAM11 protein had been forced to express, was used as a positive control [P], and it was subjected to the analysis.

Figure 4:
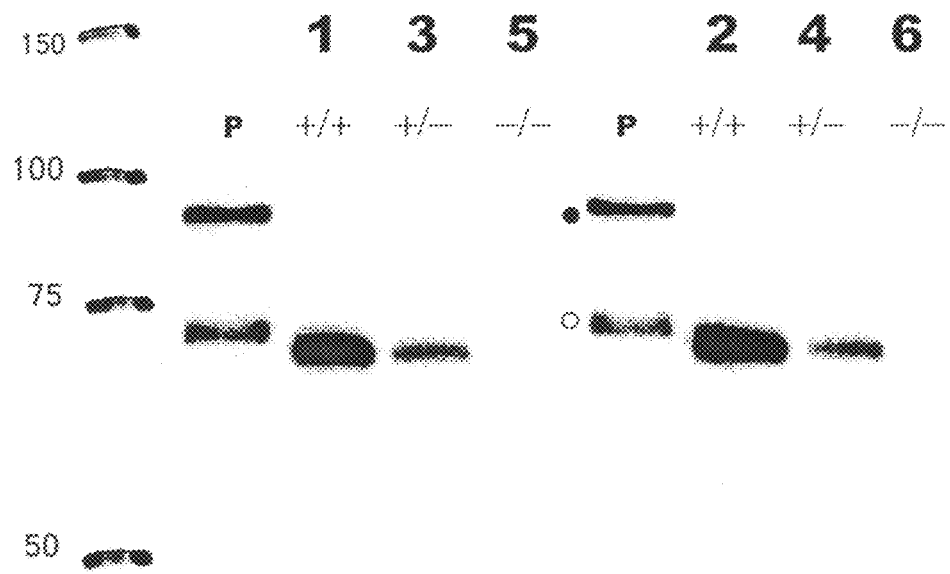
FIG. 4 shows the Western blot analysis using the cerebellum of a mouse with a disrupted ADAM11 gene.

As a result, in wild-type mice (individual numbers 1 and 2) and heterozygous mice (individual numbers 3 and 4), a single band reacting with an approximately 70-kD anti-ADAM11 antibody was detected. On the other hand, in homozygous mice (individual numbers 5 and 6), namely, in ADAM11 gene knockout mice, no bands were detected at all (FIG. 4). In the positive control, an approximately 90-kD precursor and two mature bands with a size of approximately 70 kD were detected. Only a mature band was detected in a mouse cerebellum.

From the above results, it was confirmed that no ADAM11 proteins were synthesized in the ADAM11 gene knockout mouse of the present invention.

Example 2

Test to Confirm Nervous Disorder of ADAM11 Gene Knockout Mouse 2.1: Measurement of Body Weight and Brain Weight of Mouse of Each Group The body weight, total brain weight, cerebrum weight, and cerebellum weight of each of 24-week-old male mice (8 wild-type mice, 8 hetero mice, and 8 homo mice) were measured. As a result, in terms of all of the aforementioned types of weights, no significant differences were found among the aforementioned groups (Table 1). That is, it was confirmed that appearance was not changed in each group.

TABLE 1

|  | Body weight (g) | Total brain weight (mg) | Cerebral weight (mg) | Cerebellar weight (mg) |
|---|---|---|---|---|
| Wild-type mice | 32.5 ± 0.8 | 453.8 ± 1.8 | 321.3 ± 3.0 | 43.8 ± 1.8 |
| Hetero mice | 33.3 ± 1.6 | 453.8 ± 1.8 | 323.8 ± 2.6 | 45.0 ± 1.9 |
| Homo mice | 32.8 ± 1.1 | 456.3 ± 1.8 | 320.0 ± 2.7 | 45.0 ± 1.9 |

2.2: Coordination Disorder Test (1) Measurement of Amount of Autonomic Movement

The amount of autonomic movement was measured using Versamax analysis software (Accuscan). 24-week-old male mice (8 wild-type mice, 8 hetero mice, and 8 homo mice) were placed in a Versamax cage. Soon after the placement of the mice, the total number of horizontal movements, stereotypical behaviors, and rising movements was analyzed and displayed by the analysis software. The total number (count) was used as an indicator of the amount of autonomic movement.

Figure 5:
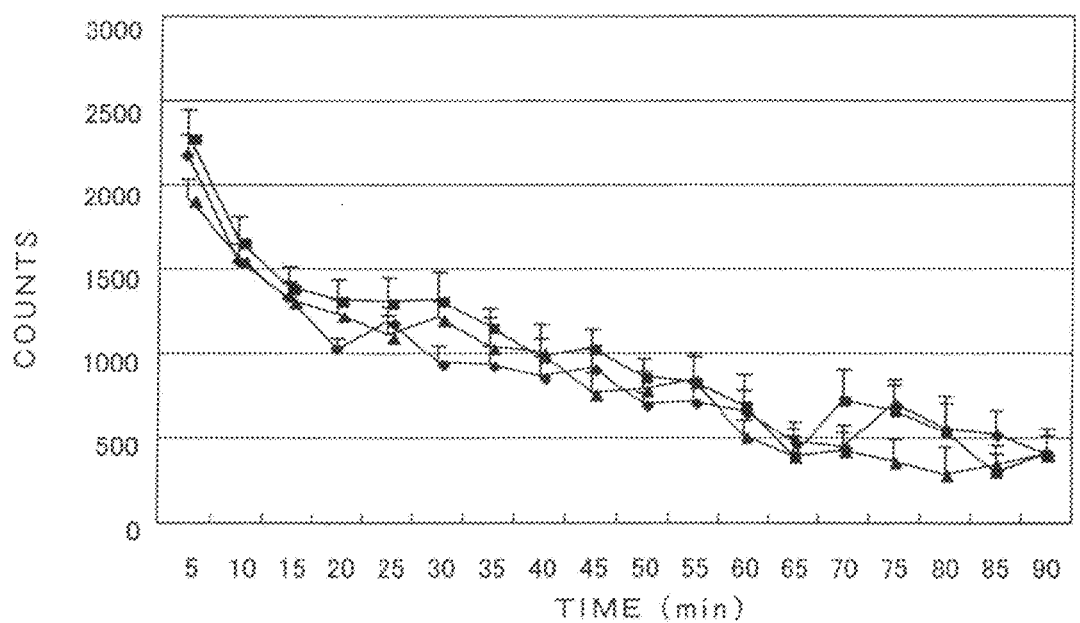
FIG. 5 shows the amount of autonomic movement (count) of each mouse group.

As a result, it was confirmed that no significant differences were observed in terms of count among the aforementioned mouse groups, and that no changes were observed in terms of the amount of autonomic movements (FIG. 5).

(2) Grip Strength (Tractional Force) Test

A grip strength (tractional force) test was carried out using a traction apparatus (FU-1, Muromachi Kikai Co., Ltd.). A portion that was 1 cm from the base of the tail of each of 24-week-old male mice (12 wild-type mice, 10 hetero mice, and 12 homo mice) was held. Thereafter, each mouse was allowed to grip with fore-legs a stainless-steel bar (diameter: 2 mm) of the traction apparatus. Thereafter, the tail was pulled, and a tractional force generated until the mouse released its fore-legs from the bar was measured.

Figure 6:
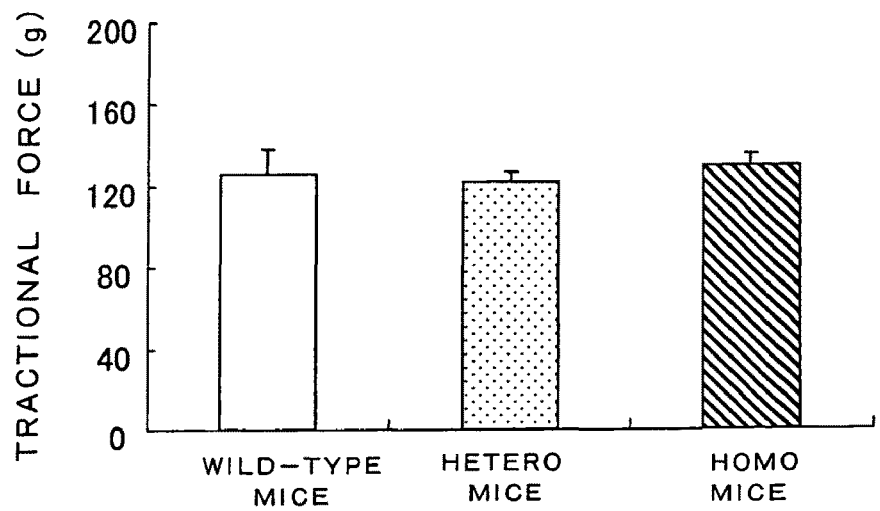
FIG. 6 shows the tractional force (grip strength) of each mouse group.

As a result, it was confirmed that no significant differences were observed among the aforementioned mouse groups, and that no changes were observed in terms of tractional force, namely, grip strength (FIG. 6).

(3) Suspension Test

A motor nerve and the muscle force of a skeleton muscle were measured by a suspension test. In this test, a stainless-steel bar (diameter: 2 mm; length: 50 cm) was placed in the horizontal direction at a height of 37 cm from the ground, and 24-week-old male mice (12 wild-type mice, 10 hetero mice, and 12 homo mice) were allowed to hang from the center of the bar with both fore-legs. Thereafter, the state of each mouse was observed for 30 seconds. The time required until the mouse fell down and a score were measured. The time and the score were used as indicators of motor nerve and the muscle power of a skeletal muscle. Scores were defined as follows: 0: the mouse immediately fell down; 1: the mouse was gripping the stainless-steel bar with its fore-legs; 2: the mouse was gripping the stainless-steel bar with its fore-legs and was attempting to chin; 3: the mouse was gripping the stainless-steel bar with its fore-legs and was also gripping the bar with at least either one hind leg; 4: the mouse was gripping the stainless-steel bar with its fore-legs and hind legs and was also twisting its tail around the bar; and 5: the mouse moved to the tip of the stainless-steel bar while keeping the state described in 4 above.

Figure 7:
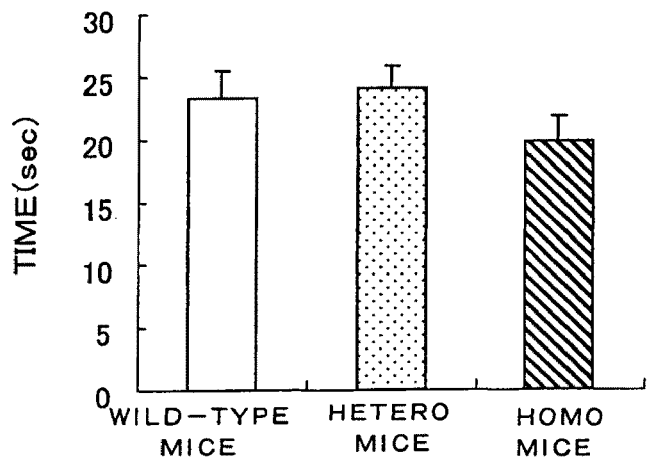
FIG. 7 shows the time required until each mouse group fell from a stainless-steel bar in a suspension test.
Figure 8:
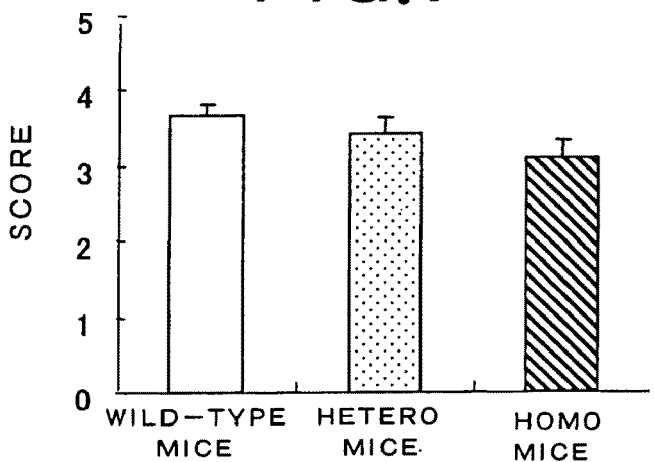
FIG. 8 shows the score of each mouse group in a suspension test.

As a result, no significant differences were found among the mice of the aforementioned groups, and it was confirmed that there were no significant changes in terms of the peripheral nerve system such as motor nerve or the muscle power of a skeleton muscle (FIGS. 7 and 8).

(4) Gait Test

Skeletal abnormality was measured by a gait test. In this test, both hind legs of each of 24-week-old male mice (12 wild-type mice, 10 hetero mice, and 12 homo mice) were painted with liquid ink. Thereafter, each mouse was allowed to walk through a passage (9×25×10 cm) in a straight line, and the width between the right and left hind legs (step width) and the strides of both hind legs (stride length) were then measured. The obtained step width and stride length were used as indicators of skeletal abnormality.

Figure 9:
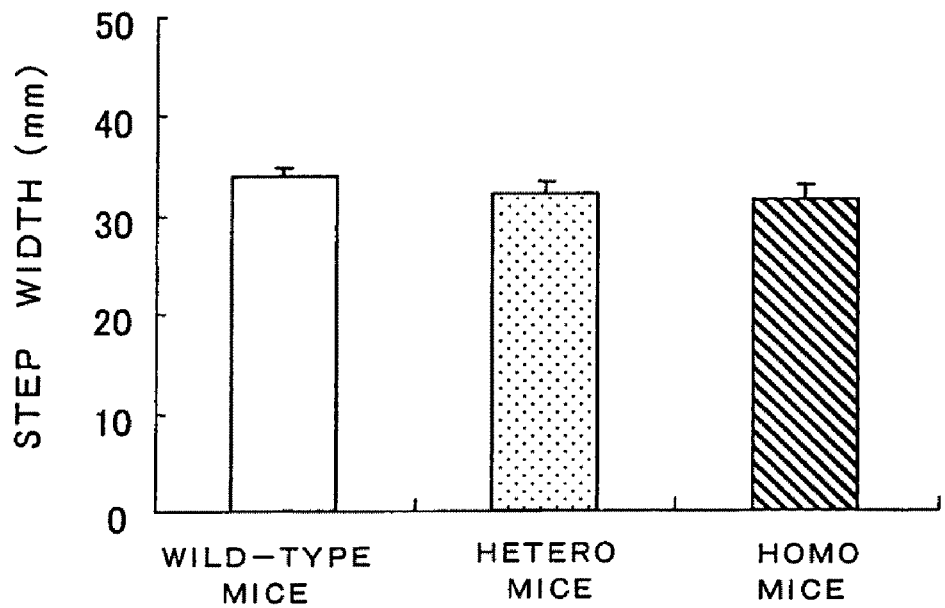
FIG. 9 shows the step width between right and left hind legs (lateral width) of each mouse group in a gait test.
Figure 10:
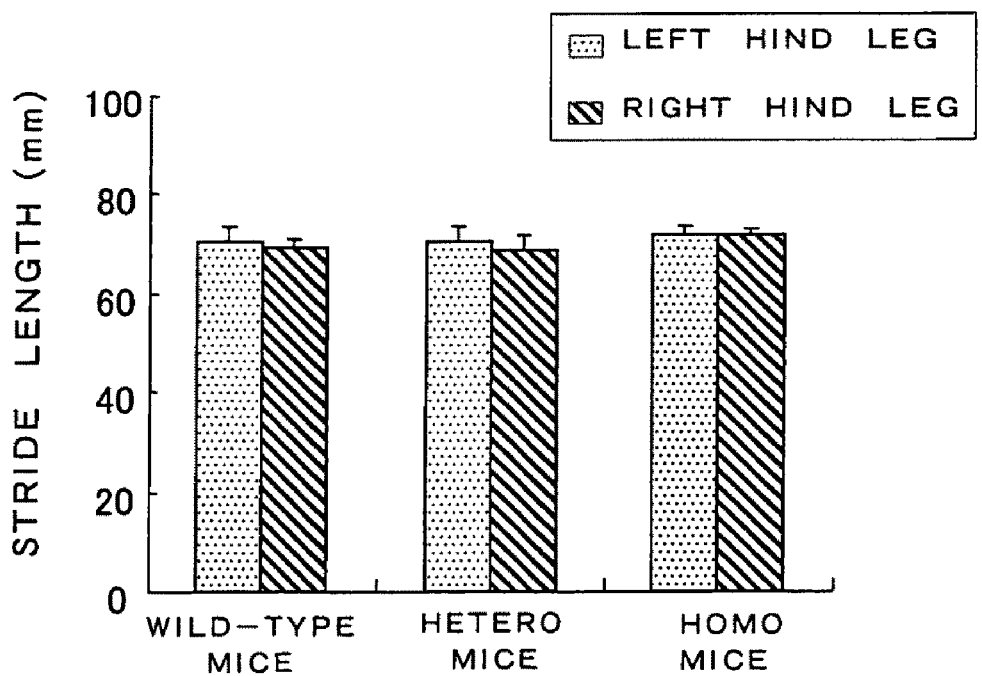
FIG. 10 shows the stride length of each of the hind legs (anteroposterior width) of each mouse group in a gait test.

As a result, no significant differences were found among the mice of the aforementioned groups, and it was confirmed that there were no significant changes in terms of the skeletal abnormality of the hind legs and leg movement during walking (FIGS. 9 and 10).

(5) Rotor Rod Test

A rotor rod test was carried out to measure incoordination. In this test, each of 24-week-old male mice (11 wild-type mice, 14 hetero mice, and 12 homo mice) was placed on a drum that was in the forth of a rotor rod (KN-75, Natsume Seisakusyo Co., Ltd.), and the drum was then rotated for 120 seconds at 0 (resting state), 5, 10, and 15 rpm. Thus, the time required until the mouse fell down from the drum was measured as a retention time, and the thus measured retention time was used as an indicator of incoordination. The number of rotation was 4 in the case of the resting state (0 rpm) and rotating at 5 rpm. The number of rotation was 8 in the case of rotating at 10 rpm, and it was 20 in the case of rotating at 15 rpm.

Figure 11:
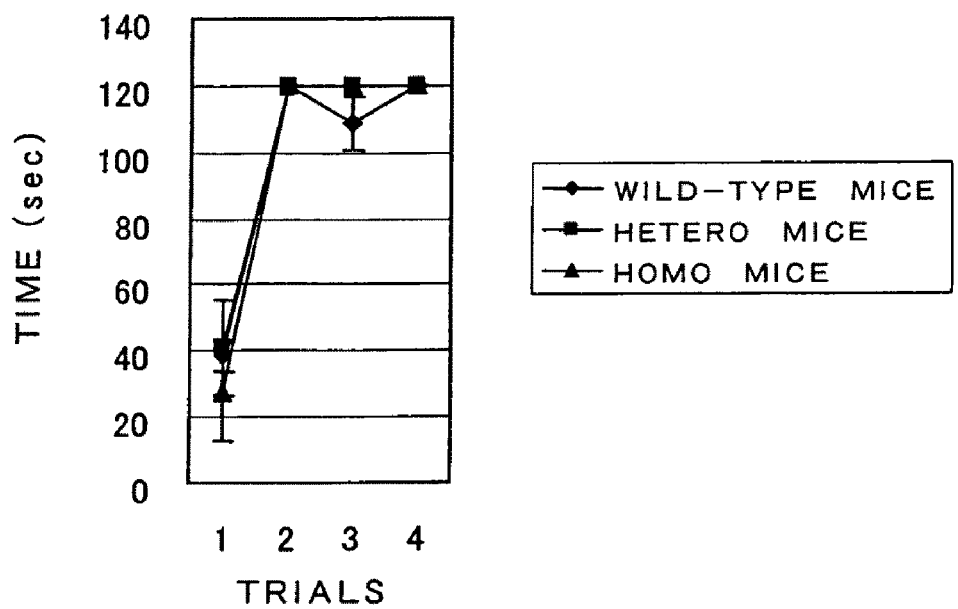
FIG. 11 shows the retention time of each mouse group in a rotor rod test (resting state).
Figure 12:
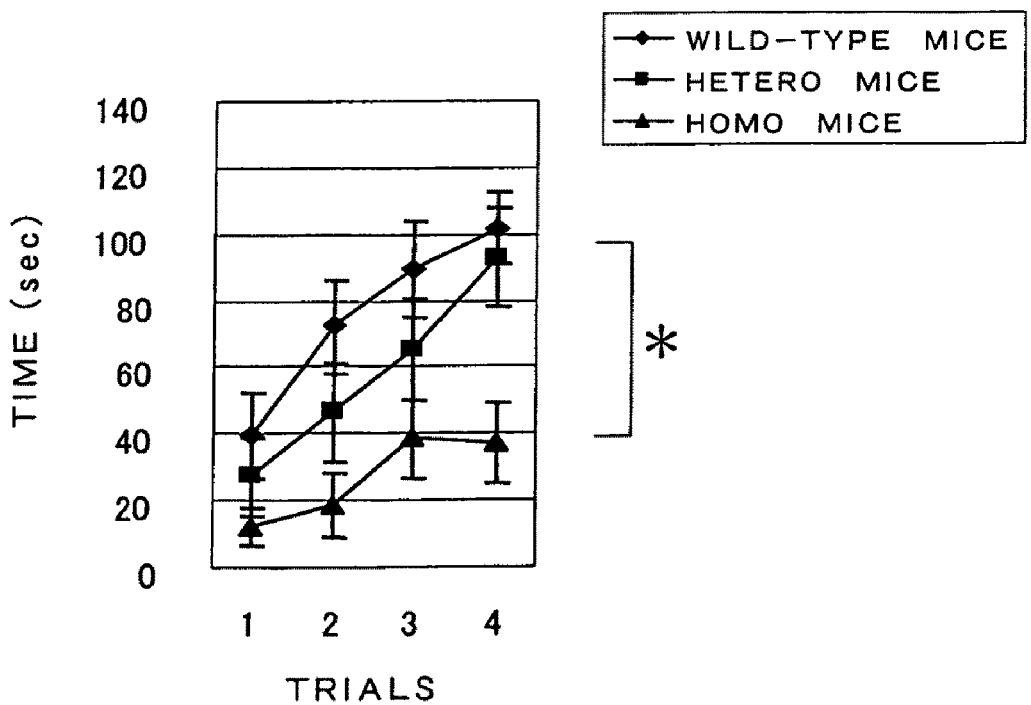
FIG. 12 shows the retention time of each mouse group in a rotor rod test (rotating at 5 rpm). In the figure, the asterisk (*) means that there is a significant difference between a homo mouse group and a wild-type mouse group (ANOVA method; $p<0.05$).
Figure 13:
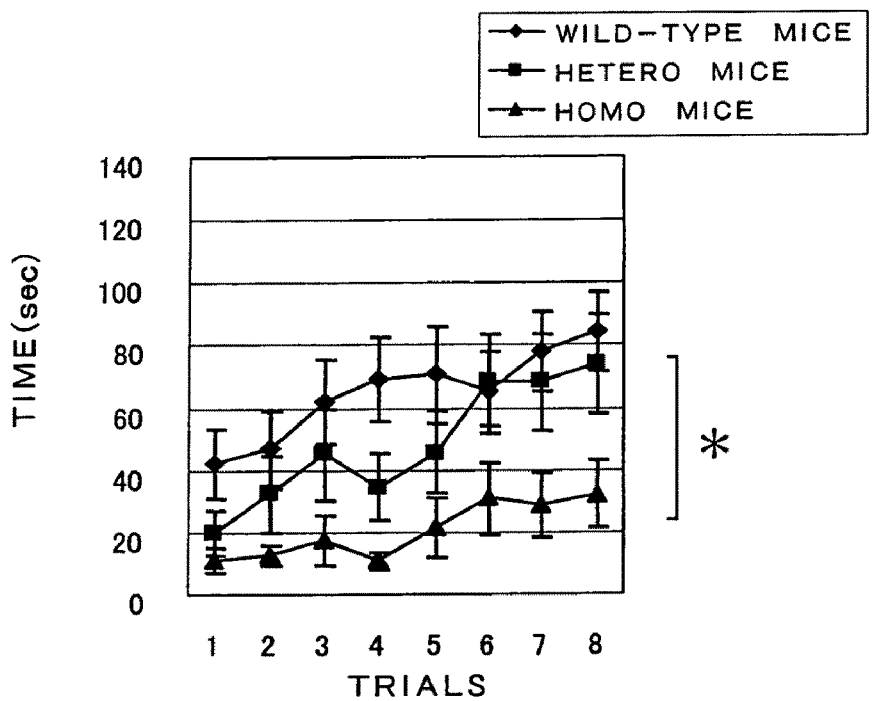
FIG. 13 shows the retention time of each mouse group in a rotor rod test (rotating at 10 rpm). In the figure, the asterisk (*) means that there is a significant difference between a homo mouse group and a wild-type mouse group (ANOVA method; $p<0.05$).
Figure 14:
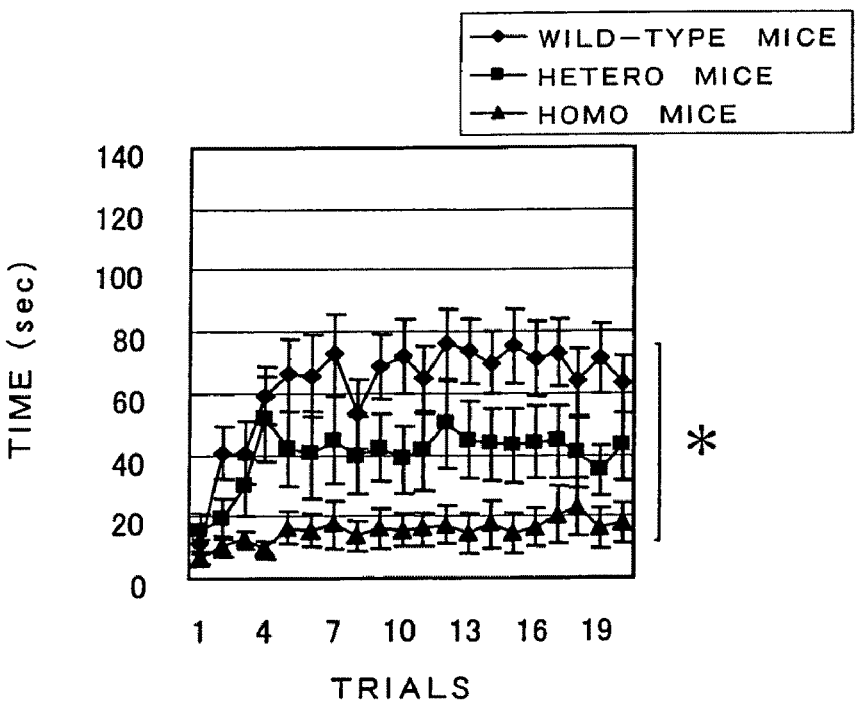
FIG. 14 shows the retention time of each mouse group in a rotor rod test (rotating at 15 rpm). In the figure, the asterisk (*) means that there is a significant difference between a homozygous mouse group and a wild-type mouse group (ANOVA method; $p<0.05$).

As a result, in the resting state, the homo mouse group was able to stay on the drum, just as with other mouse groups (FIG. 11). However, if the rotor was rotated at 5, 10, and 15 rpm, the retention time on the drum of the homo mouse group was remarkably shorter than that of the wild-type mouse group, and thus the homo mouse group was considered to suffer from incoordination (FIGS. 12 to 14). When the hetero mouse group was compared with the wild-type mouse group, no significant differences were found between the two mouse groups in the resting state and even when the rotor was rotated at 5, 10, and 15 rpm.

As a result of the aforementioned (2) grip strength (tractional force) test, (3) suspension test, and (4) gait test, no significant differences were found between the hetero mice and the homo mice, and also among the hetero mice, the homo mice, and the wild-type mice. Thus, it was confirmed that the homo mice did not have a clear injury to a peripheral nerve system such as motor nerve or muscle power, skeletal abnormity, and the like. From the aforementioned results, it is considered that incoordination of the homo mice is derived from the disorder of a central nerve system.

2.3: Memory Disorder Test

Memory disorder was measured by a water maze test.

Figure 15:
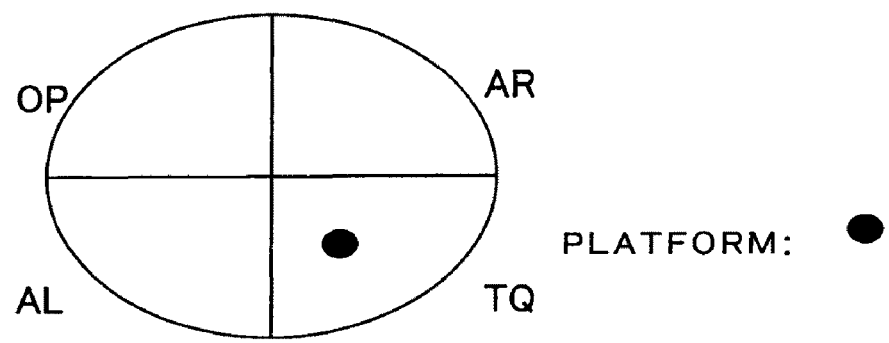
FIG. 15 shows a round pool used in the training session of a water maze test. The round pool is divided into four equal parts, and a platform is immobilized on a TQ portion.

First, each of 24-week-old male mice (11 wild-type mice, 14 hetero mice, and 12 homo mice) was learned to find out a platform (diameter: 8 cm; 1 cm below water surface) fixed below water surface in a round pool (diameter: 1.5 m; height: 30 cm) filled with water. In order to facilitate direction determination of the mouse, external visual clues (fluorescent lamps, experimental devices, wallpapers, etc.) were established around the pool, and such clues were kept constant during the experimental period. On the experimental day, the pool was divided into 4 equal parts (FIG. 15), and 4 starting points were randomly chosen. The mouse was put into water with the head towards the wall of the pool, and the latency required until the mouse evacuated to the platform was measured. When the mouse climbed to the platform, it was left as was for 15 seconds. If the mouse did not climb to the platform even after 60 seconds have passed, the test was terminated at that time, and the mouse was then placed on the platform for 15 seconds. In this case, the latency was recorded as 60 seconds. Each mouse was subjected to 1 training session per day (4 trials per session). This training session was carried out for 9 consecutive days, and the escape latency was measured. Thereafter, 24 hours after session 9 (the $9^{th}$ day), the platform was removed, and each mouse was allowed to swim for 60 seconds. The swimming route and the time at which each mouse stayed at each of the 4 equal parts were measured (probe trial (the $10^{th}$ day)). When the mouse recognized the place of the platform (TQ) and remembered it, it stayed at a site where the platform had been established for a long time. Thus, the memory of the mouse can be measured based on a retention time at each of the 4 equal parts as an indicator.

Figure 16:
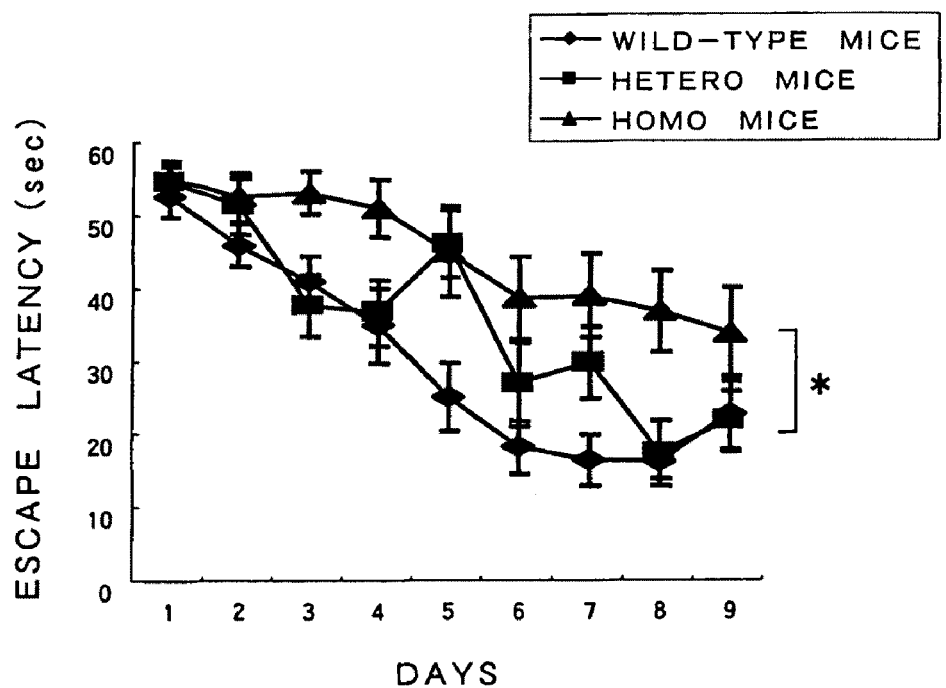
FIG. 16 shows a transition in the escape latency of each mouse group in the training session of a water maze test. In the figure, the asterisk (*) means that there is a significant difference between a homo mouse group and a wild-type mouse group (Dunnett method; $p<0.05$).
Figure 17:
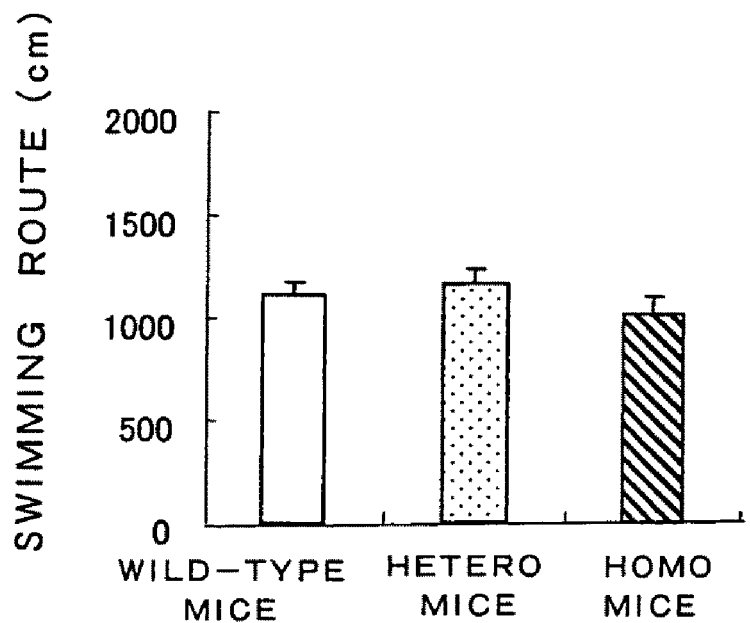
FIG. 17 shows the swimming route of each mouse group in the probe trial of a water maze test.
Figure 18:
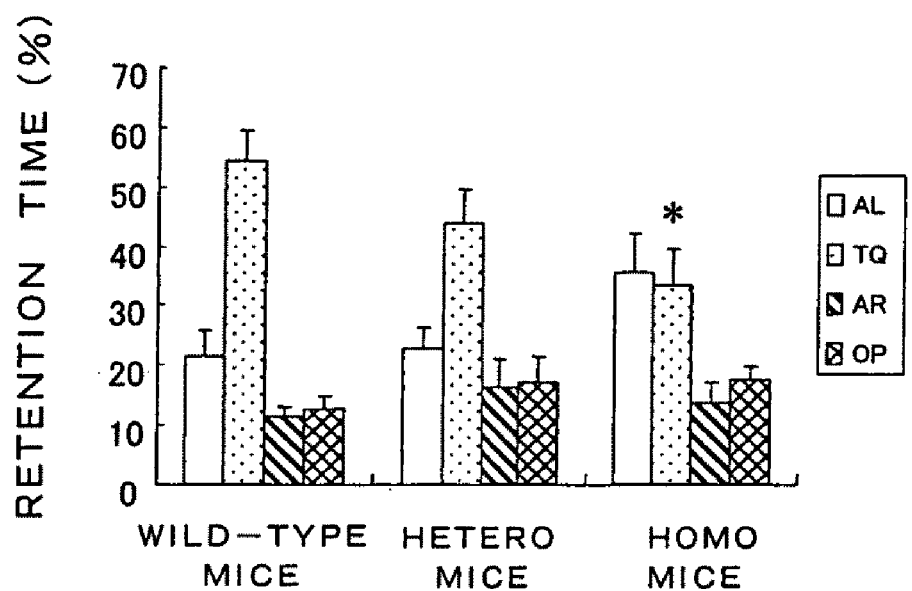
FIG. 18 shows the retention time of each mouse group at each of the four equal parts in the probe trial of a water maze test. In the figure, the asterisk (*) means that there is a significant difference between a homo mouse group and a wild-type mouse group (Dunnett method; $p<0.05$) in terms of the retention time at TQ.

As a result, a reduction in the escape latency of each group was observed in the training sessions. However, such a reduction level in the escape latency of the homo mouse group was significantly smaller than that of the wild-type mouse group. Thus, it was considered that the homo mouse group had memory disorder. On the other hand, there were no significant differences between a reduction level in the escape latency of the hetero mouse group and that of the wild-type mouse group (FIG. 16). In addition, in the probe trial, there were no significant differences in terms of the swimming route of each mouse group (FIG. 17). When the homo mouse group was compared with the wild-type mouse group, the retention time at the site where the platform (TQ) had been established was significantly short in the homo mouse group, and thus it was considered that the homo mouse group had memory disorder. On the other hand, there were no significant differences between such a retention time of the hetero mouse group and that of the wild-type mouse group (FIG. 18).

Subsequently, in order to confirm the visual ability to find out fluorescent lamps, experimental devices, wallpapers, etc., which could be clues for remembering the position of the platform located below water surface, athletic ability necessary for swimming, and spontaneity for evacuating to the platform, which were all necessary for the water maze test, the following test was carried out.

First, a flag used as a mark was set on the platform such that the swimming mouse was able to easily recognize it. On the experimental day, the position of the platform with a flag was changed for every trial, and 4 starting points were randomly chosen. The mouse was put into water with the head towards the wall of the pool, and the latency required until the mouse evacuated to the platform was measured. When the mouse climbed to the platform, it was left as was for 15 seconds. If the mouse did not climb to the platform even after 60 seconds have passed, the test was terminated at that time, and the mouse was then placed on the platform for 15 seconds. In this case, the latency was recorded as 60 seconds. Each mouse was subjected to 1 training session per day (4 trials per session). This training session was carried out for 3 consecutive days, and the escape latency was measured.

Figure 19:
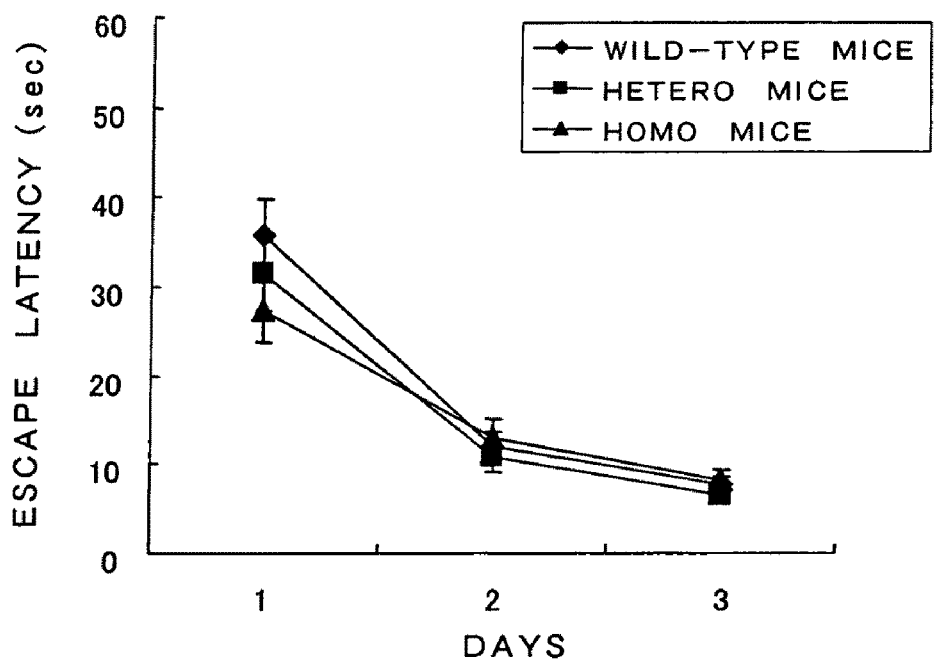
FIG. 19 shows a transition in the escape latency of each mouse group in a test in which a mark is put on a platform.

As a result, no significant differences were found among the mice of the aforementioned groups. Thus, it was confirmed that the mice of the aforementioned mouse groups had no problems regarding the visual ability, athletic ability necessary for swimming, and spontaneity for evacuating to the platform, which were all necessary for the water maze test (FIG. 19).

2.4: Paralgesia Test (1) Formalin Test

Figure 20:
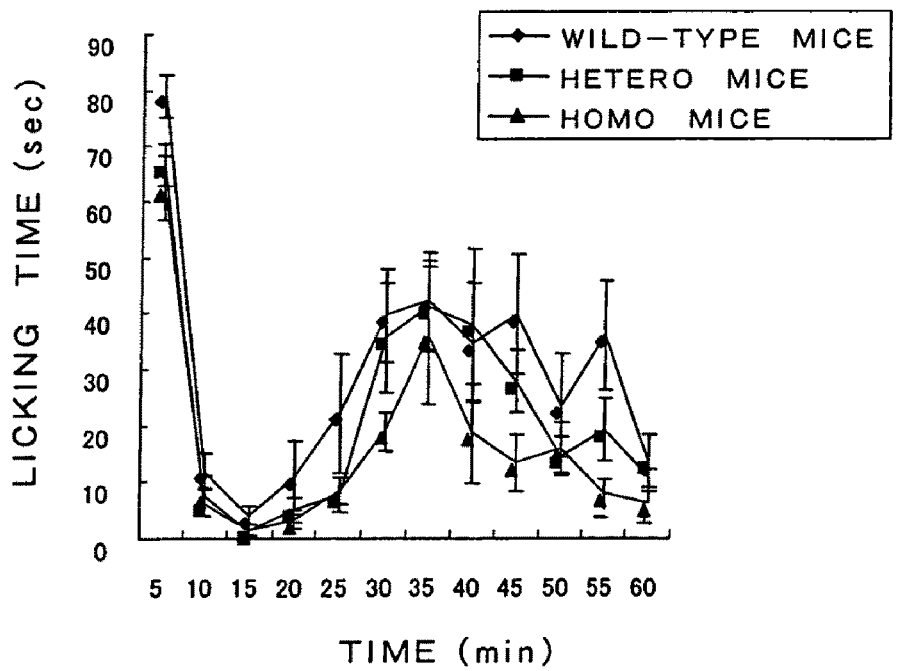
FIG. 20 shows the licking (including biting) time of each mouse group measured every 5 minutes in a formalin test.

20 µl of 3% formalin was administered to a hind foot of each of 24-week-old male mice (8 wild-type mice, 8 hetero mice, and 8 homo mice). For 60 minutes from immediately after administration of the formalin, there was measured the duration of a licking (including biting) reaction to the hind foot, which indicated the pain appearing on the hind foot, to which the formalin had been administered. The measured duration was used as an indicator of paralgesia. The measurement was carried out 12 times at intervals of 5 minutes. The licking times measured every 5 minutes are shown in FIG. 20. The appearance of such licking was divided into two phases having a boundary line as 15 minutes after administration. Thus, a phase appearing at the initial stage was defined as a first phase (0 to 5 minutes), and a phase appearing at the latter stage was defined as a second phase (15 to 60 minutes).

Figure 21:
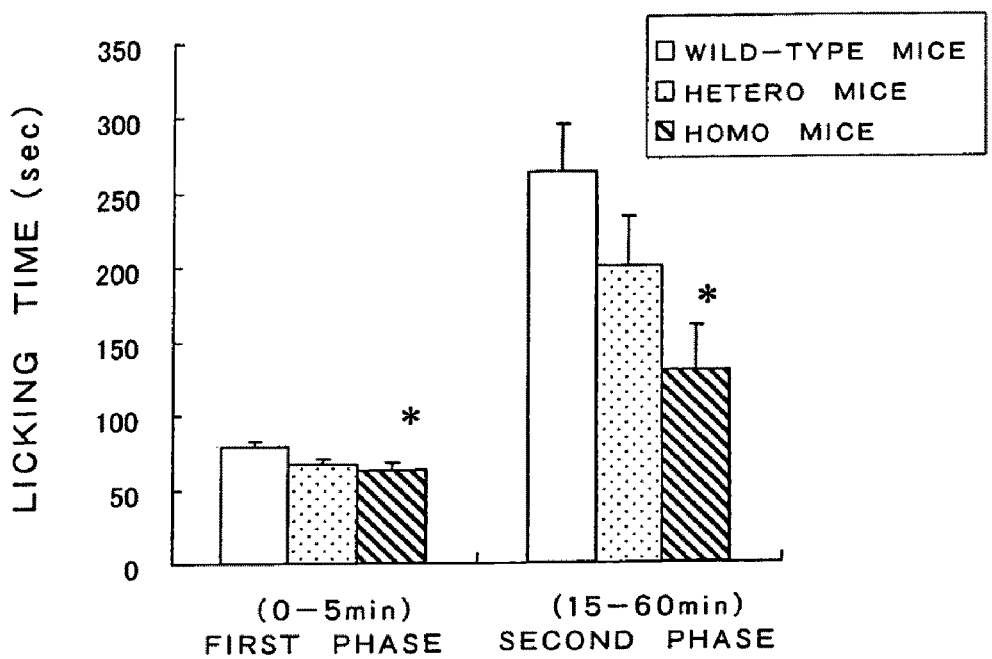
FIG. 21 shows the licking (including biting) time of each mouse group in the first and second phases of a formalin test. In the figure, the asterisk (*) means that there is a significant difference between a homo mouse group and a wild-type mouse group (Dunnett method; $p<0.05$).

As a result, in both the first and second phases, the licking time of the homo mouse group was significantly shorter than that of the wild-type mouse group, and thus it was confirmed that the homo mice suffer from paralgesia (FIG. 21).

(2) Acetic Acid Rising Test 0.6% acetic acid (10 ml/kg) was intraperitoneally administered to 24-week-old male mice (12 wild-type mice, 10 hetero mice, and 12 homo mice), which had been subjected to fasting overnight. From 10 minutes after the administration, the number of writhes such as extension of the body or hind legs or twisting its body was counted, and it was then used as an indicator of paralgesia.

Figure 22:
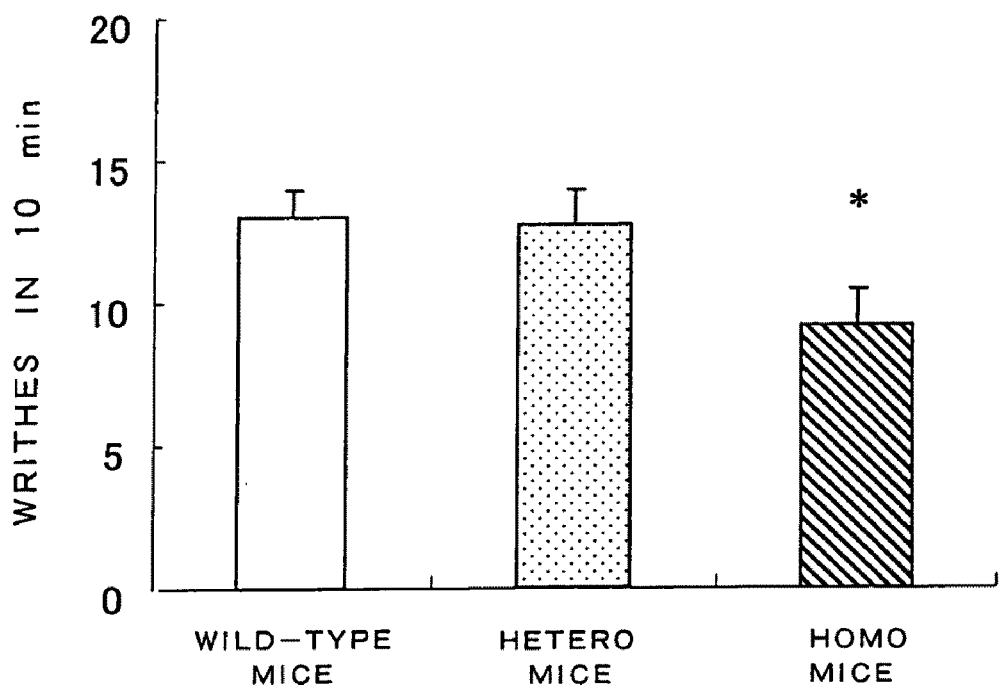
FIG. 22 shows the number of occurrence of writhes in each mouse group in an acetic acid rising method. In the figure, the asterisk (*) means that there is a significant difference between a homo mouse group and a wild-type mouse group (Dunnett method; $p<0.05$).

As a result, it was found that the number of writhes in the homo mouse group was significantly smaller than that in the wild-type mouse group, and thus it was confirmed that the homo mice suffer from paralgesia (FIG. 22).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A gene-disrupted mouse or a progeny thereof having a phenotype causing the development of a nerve-related disease, wherein the nerve-related disease is incoordination, memory disorder, agnosia, learning disability, or paralgesia, and wherein both alleles of an ADAM11 gene are disrupted by substituting at least exons 5 to 7 of both alleles of the ADAM11 gene with a foreign sequence.

2. A tissue obtained from the gene-disrupted mouse or a progeny thereof according to claim 1.

3. An animal cell obtained from the gene-disrupted mouse or a progeny thereof according to claim 1.

4. A breeding material obtained from the gene-disrupted mouse or a progeny thereof according to claim 1.

5. A method for producing the gene-disrupted mouse according to claim 1, wherein both alleles of the ADAM11 gene are disrupted, comprising the following steps:
   (a) transforming mouse embryonic stem cells (ES cells) with a polynucleotide comprising a disrupted ADAM11 gene;
   (b) selecting an ES cell, into the genome of which said polynucleotide has been incorporated;
   (c) introducing the selected ES cell into a mouse embryonic cell;
   (d) transplanting the ES cell-introduced mouse embryonic cell to the reproductive organ of a wild-type pseudopregnant female mouse, so as to reproduce a chimeric mouse;
   (e) crossing the obtained chimeric mouse with a wild-type mouse to reproduce a gene-disrupted mouse wherein either allele of the ADAM11 gene is disrupted; and
   (f) crossing a male of the obtained gene-disrupted mice with a female of the obtained gene-disrupted mice to reproduce a gene-disrupted mouse wherein both alleles of the ADAM11 gene are disrupted.

6. A method for screening for a substance used in the treatment of a nerve-related disease, a salt thereof, or a solvate thereof, comprising the following steps:
   (i) measuring the severity of a symptom of a nerve-related disease of a gene-disrupted mouse having a phenotype causing the development of a nerve-related disease selected from the group consisting of incoordination, memory disorder, agnosia, learning disability, or paralgesia, wherein both alleles of an ADAM11 gene are disrupted in a coding sequence by substituting the entire or a part of both alleles of the ADAM11 gene with a foreign sequence, wherein the disruption results in the loss of, or a reduction in, ADAM11 gene function;
   (ii) administering a test substance to said gene-disrupted mouse; and
   (iii) measuring the severity of a symptom of the nerve-related disease of said gene-disrupted mouse after administration of the test substance.

7. The screening method according to claim 6, which further comprises the following step after step (iii):
   (iv) comparing the severity of a symptom of the nerve-related disease before administration of the test substance with the severity of a symptom of the nerve-related disease after administration of the test substance.

8. The method of claim 6, wherein the disruption in both alleles of the ADAM11 gene comprises substitution of at least exons 5 to 7.

9. the method of claim 6, wherein the disruption in both alleles of the ADAM11 gene is of exons 5 to 7.

* * * * *

UNITED STATES PATENT AND TRADEMARK OFFICE
CERTIFICATE OF CORRECTION

PATENT NO. : 8,309,792 B2
APPLICATION NO. : 11/988619
DATED : November 13, 2012
INVENTOR(S) : Koji Sagane et al.

It is certified that error appears in the above-identified patent and that said Letters Patent is hereby corrected as shown below:

Title Page, (75) Inventors, replace "Turo Oki" with --Toru Oki--.

In the Specifications:

Column 8, Line 6, replace "Peasron" with --Pearson--.

Column 25, Line 5, replace "forth" with --form--.

In the Claims:

Column 60, Line 60, Claim 9, replace "the method" with --The method--.

Signed and Sealed this
Ninth Day of July, 2013

Teresa Stanek Rea
*Acting Director of the United States Patent and Trademark Office*

SEQUENCE LISTING

<160> NUMBER OF SEQ ID NOS: 13

<210> SEQ ID NO 1
<211> LENGTH: 3168
<212> TYPE: DNA
<213> ORGANISM: Homo sapiens
<220> FEATURE:
<221> NAME/KEY: CDS
<222> LOCATION: (1)..(2307)

<400> SEQUENCE: 1

```
atg agg ctg ctg cgg cgc tgg gcg ttc gcg gct ctg ctg ctg tcg ctg      48
Met Arg Leu Leu Arg Arg Trp Ala Phe Ala Ala Leu Leu Leu Ser Leu
1               5                   10                  15 ctc ccc acg ccc ggt ctt ggg acc caa ggt cct gct gga gct ctg cga      96
Leu Pro Thr Pro Gly Leu Gly Thr Gln Gly Pro Ala Gly Ala Leu Arg
                20                  25                  30 tgg ggg ggc tta ccc cag ctg gga ggc cca gga gcc cct gag gtc acg     144
Trp Gly Gly Leu Pro Gln Leu Gly Gly Pro Gly Ala Pro Glu Val Thr
            35                  40                  45 gaa ccc agc cgt ctg gtt agg gag agc tcc ggg gga gag gtc cga aag     192
Glu Pro Ser Arg Leu Val Arg Glu Ser Ser Gly Gly Glu Val Arg Lys
        50                  55                  60 cag cag ctg gac aca agg gtc cgc cag gag cca cca ggg ggc ccg cct     240
Gln Gln Leu Asp Thr Arg Val Arg Gln Glu Pro Pro Gly Gly Pro Pro
65                  70                  75                  80 gtc cat ctg gcc cag gtg agt ttc gtc atc cca gcc ttc aac tca aac     288
Val His Leu Ala Gln Val Ser Phe Val Ile Pro Ala Phe Asn Ser Asn
                85                  90                  95 ttc acc ctg gac ctg gag ctg aac cac cac ctc ctc tcc tcg caa tac     336
Phe Thr Leu Asp Leu Glu Leu Asn His His Leu Leu Ser Ser Gln Tyr
                100                 105                 110 gtg gag cgc cac ttc agc cgg gag ggg aca acc cag cac agc acc ggg     384
Val Glu Arg His Phe Ser Arg Glu Gly Thr Thr Gln His Ser Thr Gly
            115                 120                 125 gct gga gac cac tgc tac tac cag ggg aag ctc cgg ggg aac ccg cac     432
Ala Gly Asp His Cys Tyr Tyr Gln Gly Lys Leu Arg Gly Asn Pro His
        130                 135                 140 tcc ttc gcc gcc ctc tcc acc tgc cag ggg ctg cat ggg gtc ttc tct     480
Ser Phe Ala Ala Leu Ser Thr Cys Gln Gly Leu His Gly Val Phe Ser
145                 150                 155                 160 gat ggg aac ttg act tac atc gtg gag ccc caa gag gtg gct gga cct     528
Asp Gly Asn Leu Thr Tyr Ile Val Glu Pro Gln Glu Val Ala Gly Pro
                165                 170                 175 tgg gga gcc cct cag gga ccc ctt ccc cac ctc att tac cgg acc cct     576
Trp Gly Ala Pro Gln Gly Pro Leu Pro His Leu Ile Tyr Arg Thr Pro
                180                 185                 190
```

```
ctc ctc cca gat ccc ctc gga tgc agg gaa cca ggc tgc ctg ttt gct    624
Leu Leu Pro Asp Pro Leu Gly Cys Arg Glu Pro Gly Cys Leu Phe Ala
        195             200             205 gtg cct gcc cag tcg gct cct cca aac cgg ccg agg ctg aga agg aaa    672
Val Pro Ala Gln Ser Ala Pro Pro Asn Arg Pro Arg Leu Arg Arg Lys
    210             215             220 agg cag gtc cgc cgg ggc cac cct aca gtg cac agt gaa acc aag tat    720
Arg Gln Val Arg Arg Gly His Pro Thr Val His Ser Glu Thr Lys Tyr
225             230             235             240 gtg gag cta att gtg atc aac gac cac cag ctg ttc gag cag atg cga    768
Val Glu Leu Ile Val Ile Asn Asp His Gln Leu Phe Glu Gln Met Arg
                245             250             255 cag tcg gtg gtc ctc acc agc aac ttt gcc aag tcc gtg gtg aac ctg    816
Gln Ser Val Val Leu Thr Ser Asn Phe Ala Lys Ser Val Val Asn Leu
            260             265             270 gcc gat gtg ata tac aag gag cag ctc aac act cgc atc gtc ctg gtt    864
Ala Asp Val Ile Tyr Lys Glu Gln Leu Asn Thr Arg Ile Val Leu Val
        275             280             285 gcc atg gaa aca tgg gca gat ggg gac aag atc cag gtg cag gat gac    912
Ala Met Glu Thr Trp Ala Asp Gly Asp Lys Ile Gln Val Gln Asp Asp
    290             295             300 ctc ctg gag acc ctg gcc cgg ctc atg gtc tac cga cgg gag ggt ctg    960
Leu Leu Glu Thr Leu Ala Arg Leu Met Val Tyr Arg Arg Glu Gly Leu
305             310             315             320 cct gag ccc agt gat gcc acc cac ctc ttc tcg ggc agg acc ttc cag   1008
Pro Glu Pro Ser Asp Ala Thr His Leu Phe Ser Gly Arg Thr Phe Gln
                325             330             335 agc acg agc agc ggg gca gcc tac gtg ggg ggc ata tgc tcc ctg tcc   1056
Ser Thr Ser Ser Gly Ala Ala Tyr Val Gly Gly Ile Cys Ser Leu Ser
            340             345             350 cat ggc ggg ggt gtg aac gag tac ggc aac atg ggg gcg atg gcc gtg   1104
His Gly Gly Gly Val Asn Glu Tyr Gly Asn Met Gly Ala Met Ala Val
        355             360             365 acc ctt gcc cag acg ctg gga cag aac ctg ggc atg atg tgg aac aaa   1152
Thr Leu Ala Gln Thr Leu Gly Gln Asn Leu Gly Met Met Trp Asn Lys
    370             375             380 cac cgg agc tcg gca ggg gac tgc aag tgt cca gac atc tgg ctg ggc   1200
His Arg Ser Ser Ala Gly Asp Cys Lys Cys Pro Asp Ile Trp Leu Gly
385             390             395             400 tgc atc atg gag gac act ggg ttc tac ctg ccc cgc aag ttc tct cgc   1248
Cys Ile Met Glu Asp Thr Gly Phe Tyr Leu Pro Arg Lys Phe Ser Arg
                405             410             415 tgc agc atc gac gag tac aac cag ttt ctg cag gag ggt ggt ggc agc   1296
Cys Ser Ile Asp Glu Tyr Asn Gln Phe Leu Gln Glu Gly Gly Gly Ser
            420             425             430 tgc ctc ttc aac aag ccc ctc aag ctc ctg gac ccc cca gag tgc ggg   1344
Cys Leu Phe Asn Lys Pro Leu Lys Leu Leu Asp Pro Pro Glu Cys Gly
        435             440             445 aac ggc ttc gtg gag gca ggg gag gag tgc gac tgc ggc tcg gtg cag   1392
Asn Gly Phe Val Glu Ala Gly Glu Glu Cys Asp Cys Gly Ser Val Gln
    450             455             460 gag tgc agc cgc gca ggt ggc aac tgc tgc aag aaa tgc acc ctg act   1440
Glu Cys Ser Arg Ala Gly Gly Asn Cys Cys Lys Lys Cys Thr Leu Thr
465             470             475             480 cac gac gcc atg tgc agc gac ggg ctc tgc tgt cgc cgc tgc aag tac   1488
His Asp Ala Met Cys Ser Asp Gly Leu Cys Cys Arg Arg Cys Lys Tyr
                485             490             495 gaa cca cgg ggt gtg tcc tgc cga gag gcc gtg aac gag tgc gac atc   1536
Glu Pro Arg Gly Val Ser Cys Arg Glu Ala Val Asn Glu Cys Asp Ile
            500             505             510
```

```
gcg gag acc tgc acc ggg gac tct agc cag tgc ccg cct aac ctg cac      1584
Ala Glu Thr Cys Thr Gly Asp Ser Ser Gln Cys Pro Pro Asn Leu His
        515                 520                 525 aag ctg gac ggt tac tac tgt gac cat gag cag ggc cgc tgc tac gga      1632
Lys Leu Asp Gly Tyr Tyr Cys Asp His Glu Gln Gly Arg Cys Tyr Gly
    530                 535                 540 ggt cgc tgc aaa acc cgg gac cgg cag tgc cag gtt ctt tgg ggc cat      1680
Gly Arg Cys Lys Thr Arg Asp Arg Gln Cys Gln Val Leu Trp Gly His
545                 550                 555                 560 gcg gct gct gat cgc ttc tgc tac gag aag ctg aat gtg gag ggg acg      1728
Ala Ala Ala Asp Arg Phe Cys Tyr Glu Lys Leu Asn Val Glu Gly Thr
                565                 570                 575 gag cgt ggg agc tgt ggg cgc aag gga tcc ggc tgg gtc cag tgc agt      1776
Glu Arg Gly Ser Cys Gly Arg Lys Gly Ser Gly Trp Val Gln Cys Ser
    580                 585                 590 aag cag gac gtg ctg tgt ggc ttc ctc ctc tgt gtc aac atc tct gga      1824
Lys Gln Asp Val Leu Cys Gly Phe Leu Leu Cys Val Asn Ile Ser Gly
        595                 600                 605 gct cct cgg cta ggg gac ctg gtg gga gac atc agt agt gtc acc ttc      1872
Ala Pro Arg Leu Gly Asp Leu Val Gly Asp Ile Ser Ser Val Thr Phe
610                 615                 620 tac cac cag ggc aag gag ctg gac tgc agg gga ggc cac gtg cag ctg      1920
Tyr His Gln Gly Lys Glu Leu Asp Cys Arg Gly Gly His Val Gln Leu
625                 630                 635                 640 gcg gac ggc tct gac ctg agc tat gtg gag gat ggc aca gcc tgc ggg      1968
Ala Asp Gly Ser Asp Leu Ser Tyr Val Glu Asp Gly Thr Ala Cys Gly
                645                 650                 655 cct aac atg ttg tgc ctg gac cat cgc tgc ctg cca gct tct gcc ttc      2016
Pro Asn Met Leu Cys Leu Asp His Arg Cys Leu Pro Ala Ser Ala Phe
                660                 665                 670 aac ttc agc acc tgc ccc ggc agt ggg gag cgc cgg att tgc tcc cac      2064
Asn Phe Ser Thr Cys Pro Gly Ser Gly Glu Arg Arg Ile Cys Ser His
        675                 680                 685 cac ggg gtc tgc agc aat gaa ggg aag tgc atc tgt cag cca gac tgg      2112
His Gly Val Cys Ser Asn Glu Gly Lys Cys Ile Cys Gln Pro Asp Trp
    690                 695                 700 aca ggc aaa gac tgc agt atc cat aac ccc ctg ccc acg tcc cca ccc      2160
Thr Gly Lys Asp Cys Ser Ile His Asn Pro Leu Pro Thr Ser Pro Pro
705                 710                 715                 720 acg ggg gag acg gag aga tat aaa ggt ccc agc ggc acc aac atc atc      2208
Thr Gly Glu Thr Glu Arg Tyr Lys Gly Pro Ser Gly Thr Asn Ile Ile
                725                 730                 735 att ggc tcc atc gct ggg gct gtc ctg gtt gca gcc atc gtc ctg ggc      2256
Ile Gly Ser Ile Ala Gly Ala Val Leu Val Ala Ala Ile Val Leu Gly
                740                 745                 750 ggc acg ggc tgg gga ttt aaa aac att cgc cga gga agg tcc gga ggg      2304
Gly Thr Gly Trp Gly Phe Lys Asn Ile Arg Arg Gly Arg Ser Gly Gly
        755                 760                 765 gcc taagtgccac cctcctccct ccaagcctgg cacccaccgt ctcggccctg            2357
Ala aaccacgagg ctgcccccat ccagccacgg agggaggcac catgcaaatg tcttccaggt    2417 ccaaacccctt caactcctgg ctccgcaggg gtttgggtgg gggctgtggc cctgcccttg   2477
gcaccaccag ggtggaccag gcctggaggg cacttcctcc acagtccccc acccacctcc    2537
tgcggctcag ccttgcacac ccactgcccc gtgtgaatgt agcttccacc tcatggattg    2597
ccacagctca actcgggggc acctggaggg atgcccccag gcagccacca gtggacctag    2657 cctgatggc ccctccttgc aaccaggcag ctgagaccag ggtcttatct ctctgggacc     2717 taggggacg gggctgacat ctacattttt taaaactgaa tcttaatcga tgaatgtaaa     2777
```

```
ctcgggggtg ctggggccag ggcagatgtg gggatgtttt gacatttaca ggaggccccg    2837
gagaaactga ggtatggcca tgccctagac cctccccaag gatgaccaca cccgaagtcc    2897
tgtcactgag cacagtcagg ggctgggcat cccagcttgc ccccgcttag ccccgctgag    2957
cttggaggaa gtatgagtgc tgattcaaac caaagctgcc tgtgccatgc ccaaggccta    3017
ggttatgggt acggcaacca catgtcccag atcgtctcca attcgaaaac aaccgtcctg    3077 ctgtcccctgt caggacacat ggattttggc agggcggggg ggggttctag aaaatatagg    3137
ttcctataat aaaatggcac cttccccctt t                                    3168
```

<210> SEQ ID NO 2
<211> LENGTH: 769
<212> TYPE: PRT
<213> ORGANISM: Homo sapiens

<400> SEQUENCE: 2

```
Met Arg Leu Leu Arg Arg Trp Ala Phe Ala Ala Leu Leu Ser Leu
1               5                   10                  15

Leu Pro Thr Pro Gly Leu Gly Thr Gln Gly Pro Ala Gly Ala Leu Arg
            20                  25                  30

Trp Gly Gly Leu Pro Gln Leu Gly Gly Pro Gly Ala Pro Glu Val Thr
        35                  40                  45

Glu Pro Ser Arg Leu Val Arg Glu Ser Ser Gly Gly Glu Val Arg Lys
    50                  55                  60

Gln Gln Leu Asp Thr Arg Val Arg Gln Glu Pro Pro Gly Gly Pro Pro
65                  70                  75                  80

Val His Leu Ala Gln Val Ser Phe Val Ile Pro Ala Phe Asn Ser Asn
                85                  90                  95

Phe Thr Leu Asp Leu Glu Leu Asn His His Leu Leu Ser Ser Gln Tyr
                100                 105                 110

Val Glu Arg His Phe Ser Arg Glu Gly Thr Thr Gln His Ser Thr Gly
            115                 120                 125

Ala Gly Asp His Cys Tyr Tyr Gln Gly Lys Leu Arg Gly Asn Pro His
        130                 135                 140

Ser Phe Ala Ala Leu Ser Thr Cys Gln Gly Leu His Gly Val Phe Ser
145                 150                 155                 160

Asp Gly Asn Leu Thr Tyr Ile Val Glu Pro Gln Glu Val Ala Gly Pro
                165                 170                 175

Trp Gly Ala Pro Gln Gly Pro Leu Pro His Leu Ile Tyr Arg Thr Pro
            180                 185                 190

Leu Leu Pro Asp Pro Leu Gly Cys Arg Glu Pro Gly Cys Leu Phe Ala
        195                 200                 205

Val Pro Ala Gln Ser Ala Pro Pro Asn Arg Pro Arg Leu Arg Arg Lys
    210                 215                 220

Arg Gln Val Arg Arg Gly His Pro Thr Val His Ser Glu Thr Lys Tyr
225                 230                 235                 240

Val Glu Leu Ile Val Ile Asn Asp His Gln Leu Phe Glu Gln Met Arg
                245                 250                 255

Gln Ser Val Val Leu Thr Ser Asn Phe Ala Lys Ser Val Val Asn Leu
            260                 265                 270

Ala Asp Val Ile Tyr Lys Glu Gln Leu Asn Thr Arg Ile Val Leu Val
        275                 280                 285

Ala Met Glu Thr Trp Ala Asp Gly Asp Lys Ile Gln Val Gln Asp Asp
    290                 295                 300
```

-continued

```
Leu Leu Glu Thr Leu Ala Arg Leu Met Val Tyr Arg Arg Glu Gly Leu
305                 310                 315                 320

Pro Glu Pro Ser Asp Ala Thr His Leu Phe Ser Gly Arg Thr Phe Gln
            325                 330                 335

Ser Thr Ser Ser Gly Ala Ala Tyr Val Gly Gly Ile Cys Ser Leu Ser
        340                 345                 350

His Gly Gly Gly Val Asn Glu Tyr Gly Asn Met Gly Ala Met Ala Val
    355                 360                 365

Thr Leu Ala Gln Thr Leu Gly Gln Asn Leu Gly Met Met Trp Asn Lys
370                 375                 380

His Arg Ser Ser Ala Gly Asp Cys Lys Cys Pro Asp Ile Trp Leu Gly
385                 390                 395                 400

Cys Ile Met Glu Asp Thr Gly Phe Tyr Leu Pro Arg Lys Phe Ser Arg
                405                 410                 415

Cys Ser Ile Asp Glu Tyr Asn Gln Phe Leu Gln Glu Gly Gly Gly Ser
            420                 425                 430

Cys Leu Phe Asn Lys Pro Leu Lys Leu Leu Asp Pro Glu Cys Gly
                435                 440                 445

Asn Gly Phe Val Glu Ala Gly Glu Glu Cys Asp Cys Gly Ser Val Gln
450                 455                 460

Glu Cys Ser Arg Ala Gly Gly Asn Cys Cys Lys Lys Cys Thr Leu Thr
465                 470                 475                 480

His Asp Ala Met Cys Ser Asp Gly Leu Cys Cys Arg Arg Cys Lys Tyr
                485                 490                 495

Glu Pro Arg Gly Val Ser Cys Arg Glu Ala Val Asn Glu Cys Asp Ile
            500                 505                 510

Ala Glu Thr Cys Thr Gly Asp Ser Ser Gln Cys Pro Pro Asn Leu His
    515                 520                 525

Lys Leu Asp Gly Tyr Tyr Cys Asp His Glu Gln Gly Arg Cys Tyr Gly
    530                 535                 540

Gly Arg Cys Lys Thr Arg Asp Arg Gln Cys Gln Val Leu Trp Gly His
545                 550                 555                 560

Ala Ala Ala Asp Arg Phe Cys Tyr Glu Lys Leu Asn Val Glu Gly Thr
                565                 570                 575

Glu Arg Gly Ser Cys Gly Arg Lys Gly Ser Gly Trp Val Gln Cys Ser
            580                 585                 590

Lys Gln Asp Val Leu Cys Gly Phe Leu Leu Cys Val Asn Ile Ser Gly
                595                 600                 605

Ala Pro Arg Leu Gly Asp Leu Val Gly Asp Ile Ser Ser Val Thr Phe
    610                 615                 620

Tyr His Gln Gly Lys Glu Leu Asp Cys Arg Gly Gly His Val Gln Leu
625                 630                 635                 640

Ala Asp Gly Ser Asp Leu Ser Tyr Val Glu Asp Gly Thr Ala Cys Gly
                645                 650                 655

Pro Asn Met Leu Cys Leu Asp His Arg Cys Leu Pro Ala Ser Ala Phe
            660                 665                 670

Asn Phe Ser Thr Cys Pro Gly Ser Gly Glu Arg Arg Ile Cys Ser His
                675                 680                 685

His Gly Val Cys Ser Asn Glu Gly Lys Cys Ile Cys Gln Pro Asp Trp
    690                 695                 700

Thr Gly Lys Asp Cys Ser Ile His Asn Pro Leu Pro Thr Ser Pro Pro
705                 710                 715                 720

Thr Gly Glu Thr Glu Arg Tyr Lys Gly Pro Ser Gly Thr Asn Ile Ile
                725                 730                 735
```

```
Ile Gly Ser Ile Ala Gly Ala Val Leu Val Ala Ala Ile Val Leu Gly
                740                 745                 750

Gly Thr Gly Trp Gly Phe Lys Asn Ile Arg Arg Gly Arg Ser Gly Gly
            755                 760                 765

Ala

<210> SEQ ID NO 3
<211> LENGTH: 3214
<212> TYPE: DNA
<213> ORGANISM: Mus musculus
<220> FEATURE:
<221> NAME/KEY: CDS
<222> LOCATION: (1)..(2319)
<220> FEATURE:
<221> NAME/KEY: misc_feature
<222> LOCATION: (1)..(3214)
<223> OTHER INFORMATION: The expression "n" at nucleotides 2753, 2755,
      2757, 2759, 2761, 2763, 2765, 2767, 2769, 2771, and 2773 may be
      any one of G, C, T, and A, respectively.

<400> SEQUENCE: 3 atg agg cgg ctg cgg cgc tgg gcg atc gcg gct ctg ctg ctg tta ccg        48
Met Arg Arg Leu Arg Arg Trp Ala Ile Ala Ala Leu Leu Leu Leu Pro
1               5                   10                  15 ctt ctc ccc ccg ccc ggt ctt ggg gcc ctg ggt ccc aga gga gct ctg        96
Leu Leu Pro Pro Pro Gly Leu Gly Ala Leu Gly Pro Arg Gly Ala Leu
                20                  25                  30 cac tgg agg agc tca gcc cat gtg ggg agc cca gag agt cca gag ggc       144
His Trp Arg Ser Ser Ala His Val Gly Ser Pro Glu Ser Pro Glu Gly
            35                  40                  45 tct gag gtc aca gag ccc agc cgg ctg gta agg cag agc tcc ggg gga       192
Ser Glu Val Thr Glu Pro Ser Arg Leu Val Arg Gln Ser Ser Gly Gly
        50                  55                  60 gag gtc cga aag cca cag ttg gac acc agg gtc cgc cag gat ccg ccc       240
Glu Val Arg Lys Pro Gln Leu Asp Thr Arg Val Arg Gln Asp Pro Pro
65                  70                  75                  80 agg ggg acg cct gtg cac ctg gcc cag gtg agt ttc gtc atc ccg gcc       288
Arg Gly Thr Pro Val His Leu Ala Gln Val Ser Phe Val Ile Pro Ala
                85                  90                  95 ttc gac tca aac ttc act ctg gac ctg gag ctg aac cat cac ctc ctg       336
Phe Asp Ser Asn Phe Thr Leu Asp Leu Glu Leu Asn His His Leu Leu
                100                 105                 110 tcc tcg cag tat gtg gag cgc cac ttc agc cgg gag gga aca aga caa       384
Ser Ser Gln Tyr Val Glu Arg His Phe Ser Arg Glu Gly Thr Arg Gln
            115                 120                 125 cac agc act ggg gct gga gac cac tgc tac tac cat ggg aaa ctc cgg       432
His Ser Thr Gly Ala Gly Asp His Cys Tyr Tyr His Gly Lys Leu Arg
        130                 135                 140 ggc aac cca cag tcc ttt gct gca ctc tct aca tgc cag ggg ctg cat       480
Gly Asn Pro Gln Ser Phe Ala Ala Leu Ser Thr Cys Gln Gly Leu His
145                 150                 155                 160 ggg gtc ttc tct gat ggc aac ctg act tac atc gta gag cct aag gag       528
Gly Val Phe Ser Asp Gly Asn Leu Thr Tyr Ile Val Glu Pro Lys Glu
                165                 170                 175 ata gct ggg ccc cgg gga ccc cca cag gga ccc ctt ccc cac ctc att       576
Ile Ala Gly Pro Arg Gly Pro Pro Gln Gly Pro Leu Pro His Leu Ile
                180                 185                 190 tac cgg acc cct ctc ctc cca gcc ccc ctt gga tgc agg gag cca ggc       624
Tyr Arg Thr Pro Leu Leu Pro Ala Pro Leu Gly Cys Arg Glu Pro Gly
            195                 200                 205 tgc ctg ttt gct gtc cct gcc cag tct act ctc ccc aac tgg ccc aag       672
Cys Leu Phe Ala Val Pro Ala Gln Ser Thr Leu Pro Asn Trp Pro Lys
        210                 215                 220
```

```
cta aga agg aaa agg cag gtc cgc agg ggc cac ccc aca gtg cac agc      720
Leu Arg Arg Lys Arg Gln Val Arg Arg Gly His Pro Thr Val His Ser
225                 230                 235                 240 gag acc aag tat gtg gag ttg att gta atc aat gac cac cag ctg ttt      768
Glu Thr Lys Tyr Val Glu Leu Ile Val Ile Asn Asp His Gln Leu Phe
                245                 250                 255 gag cag atg cgg cag tca gtg gtc ctc acc agc aac ttt gca aaa tct      816
Glu Gln Met Arg Gln Ser Val Val Leu Thr Ser Asn Phe Ala Lys Ser
            260                 265                 270 gtt gtg aac ctg gca gat gtg ata tac aag gaa cag ctc aac aca aga      864
Val Val Asn Leu Ala Asp Val Ile Tyr Lys Glu Gln Leu Asn Thr Arg
        275                 280                 285 att gtt ctg gtt gcc atg gaa acg tgg gca gat ggg gac aag atc cag      912
Ile Val Leu Val Ala Met Glu Thr Trp Ala Asp Gly Asp Lys Ile Gln
    290                 295                 300 gtg cag gat gac cta ctg gag acc ctg gcc cgg ctt atg gtc tac cgg      960
Val Gln Asp Asp Leu Leu Glu Thr Leu Ala Arg Leu Met Val Tyr Arg
305                 310                 315                 320 cgg gag ggt ctg cct gag ccc agt gat gcc acc cac ctc ttc tcg ggt     1008
Arg Glu Gly Leu Pro Glu Pro Ser Asp Ala Thr His Leu Phe Ser Gly
                325                 330                 335 aga acc ttc aag agc acc agc agc ggg gcg gcc tac gtg gga ggc atc     1056
Arg Thr Phe Lys Ser Thr Ser Ser Gly Ala Ala Tyr Val Gly Gly Ile
            340                 345                 350 tgt tca ctg tcc cgg ggt gga ggt gtg aac gag tat ggc aac atg ggt     1104
Cys Ser Leu Ser Arg Gly Gly Gly Val Asn Glu Tyr Gly Asn Met Gly
        355                 360                 365 gcc atg gcg gtg acc ctg gcc cag acg cta ggg cag aac ttg ggc atg     1152
Ala Met Ala Val Thr Leu Ala Gln Thr Leu Gly Gln Asn Leu Gly Met
    370                 375                 380 atg tgg aat aag cac cgg agc tca gca ggg gac tgc aag tgt cca gac     1200
Met Trp Asn Lys His Arg Ser Ser Ala Gly Asp Cys Lys Cys Pro Asp
385                 390                 395                 400 att tgg ctg ggc tgc atc atg gag gac act ggg ttc tat ttg ccc cgc     1248
Ile Trp Leu Gly Cys Ile Met Glu Asp Thr Gly Phe Tyr Leu Pro Arg
                405                 410                 415 aag ttc tcg cgc tgc agc atc gac gaa tac aac cag ttt ctg cag gag     1296
Lys Phe Ser Arg Cys Ser Ile Asp Glu Tyr Asn Gln Phe Leu Gln Glu
            420                 425                 430 gga ggc ggg agc tgc ctg ttc aac aag ccc ctc aag ctt ctg gac cct     1344
Gly Gly Gly Ser Cys Leu Phe Asn Lys Pro Leu Lys Leu Leu Asp Pro
        435                 440                 445 ccc gag tgc gga aac ggc ttc gtg gag gcg gga gag gag tgc gac tgc     1392
Pro Glu Cys Gly Asn Gly Phe Val Glu Ala Gly Glu Glu Cys Asp Cys
    450                 455                 460 ggg tcg gtg cag gag tgc agc cga gca ggg ggc aac tgc tgc aaa aaa     1440
Gly Ser Val Gln Glu Cys Ser Arg Ala Gly Gly Asn Cys Cys Lys Lys
465                 470                 475                 480 tgc acc ttg acg cac gac gcc atg tgc agc gat ggg ctc tgt tgt cgc     1488
Cys Thr Leu Thr His Asp Ala Met Cys Ser Asp Gly Leu Cys Cys Arg
                485                 490                 495 cgc tgc aag tat gag cca cga ggt gtc tcc tgc cga gaa gcg gtg aat     1536
Arg Cys Lys Tyr Glu Pro Arg Gly Val Ser Cys Arg Glu Ala Val Asn
            500                 505                 510 gag tgt gac att gca gag acc tgc acc ggc gac tca agc cag tgt ccc     1584
Glu Cys Asp Ile Ala Glu Thr Cys Thr Gly Asp Ser Ser Gln Cys Pro
        515                 520                 525 cct aac ctt cac aag ctg gac ggt tac tac tgt gat cat gag cag ggt     1632
Pro Asn Leu His Lys Leu Asp Gly Tyr Tyr Cys Asp His Glu Gln Gly
    530                 535                 540
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cgt | tgc | tat | gga | ggc | cgc | tgt | aaa | acc | cgg | gac | cgg | cag | tgc | caa | gcc | 1680 |
| Arg | Cys | Tyr | Gly | Gly | Arg | Cys | Lys | Thr | Arg | Asp | Arg | Gln | Cys | Gln | Ala |      |
| 545 |     |     |     | 550 |     |     |     |     | 555 |     |     |     |     | 560 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cta | tgg | ggc | cat | gcg | gct | gcg | gat | cgt | ttc | tgc | tat | gag | aag | ctg | aac | 1728 |
| Leu | Trp | Gly | His | Ala | Ala | Ala | Asp | Arg | Phe | Cys | Tyr | Glu | Lys | Leu | Asn |      |
|     |     |     |     | 565 |     |     |     |     | 570 |     |     |     |     | 575 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | gag | ggg | aca | gag | cgt | gga | aac | tgt | gga | cgc | aag | gga | tct | ggt | tgg | 1776 |
| Val | Glu | Gly | Thr | Glu | Arg | Gly | Asn | Cys | Gly | Arg | Lys | Gly | Ser | Gly | Trp |      |
|     |     |     |     | 580 |     |     |     |     | 585 |     |     |     |     | 590 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtc | cag | tgc | agt | aag | cag | gat | gtg | ctc | tgt | ggc | ttc | ctt | ctg | tgc | gtc | 1824 |
| Val | Gln | Cys | Ser | Lys | Gln | Asp | Val | Leu | Cys | Gly | Phe | Leu | Leu | Cys | Val |      |
|     |     |     |     | 595 |     |     |     |     | 600 |     |     |     |     | 605 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | atc | tct | gga | gct | ccg | cgg | cta | ggg | gat | ctg | ggg | ggc | gac | atc | agc | 1872 |
| Asn | Ile | Ser | Gly | Ala | Pro | Arg | Leu | Gly | Asp | Leu | Gly | Gly | Asp | Ile | Ser |      |
| 610 |     |     |     |     | 615 |     |     |     |     | 620 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agt | gtc | acc | ttc | tac | cac | cag | ggc | aag | gag | ttg | gac | tgc | agg | gga | ggc | 1920 |
| Ser | Val | Thr | Phe | Tyr | His | Gln | Gly | Lys | Glu | Leu | Asp | Cys | Arg | Gly | Gly |      |
| 625 |     |     |     |     | 630 |     |     |     |     | 635 |     |     |     |     | 640 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cac | gtg | cag | cta | gct | gat | ggc | tcg | gac | ctg | agc | tat | gtg | gag | gac | ggc | 1968 |
| His | Val | Gln | Leu | Ala | Asp | Gly | Ser | Asp | Leu | Ser | Tyr | Val | Glu | Asp | Gly |      |
|     |     |     |     | 645 |     |     |     |     | 650 |     |     |     |     | 655 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acg | gcc | tgt | ggg | ccc | aac | atg | ttg | tgc | cta | gat | cac | cgc | tgc | ctg | cca | 2016 |
| Thr | Ala | Cys | Gly | Pro | Asn | Met | Leu | Cys | Leu | Asp | His | Arg | Cys | Leu | Pro |      |
|     |     |     |     | 660 |     |     |     |     | 665 |     |     |     |     | 670 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | tct | gcc | ttc | aac | ttc | agc | acc | tgc | cct | gga | agt | gga | gag | cga | agg | 2064 |
| Ala | Ser | Ala | Phe | Asn | Phe | Ser | Thr | Cys | Pro | Gly | Ser | Gly | Glu | Arg | Arg |      |
|     |     |     |     | 675 |     |     |     |     | 680 |     |     |     |     | 685 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | tgc | tcc | cat | cat | ggg | gtt | tgc | agc | aac | gag | ggg | aag | tgt | atc | tgt | 2112 |
| Ile | Cys | Ser | His | His | Gly | Val | Cys | Ser | Asn | Glu | Gly | Lys | Cys | Ile | Cys |      |
|     |     |     |     | 690 |     |     |     |     | 695 |     |     |     |     | 700 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cag | cca | gac | tgg | aca | ggc | aaa | gac | tgc | agt | att | cac | aac | cca | ctg | ccc | 2160 |
| Gln | Pro | Asp | Trp | Thr | Gly | Lys | Asp | Cys | Ser | Ile | His | Asn | Pro | Leu | Pro |      |
| 705 |     |     |     |     | 710 |     |     |     |     | 715 |     |     |     |     | 720 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acg | tcc | cct | ccc | act | ggg | gag | act | gag | aga | tac | aaa | ggt | ccc | agc | ggt | 2208 |
| Thr | Ser | Pro | Pro | Thr | Gly | Glu | Thr | Glu | Arg | Tyr | Lys | Gly | Pro | Ser | Gly |      |
|     |     |     |     | 725 |     |     |     |     | 730 |     |     |     |     | 735 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | aac | atc | atc | att | ggc | tcc | atc | gcc | ggg | gct | gtc | ctg | gtc | gca | gcc | 2256 |
| Thr | Asn | Ile | Ile | Ile | Gly | Ser | Ile | Ala | Gly | Ala | Val | Leu | Val | Ala | Ala |      |
|     |     |     |     | 740 |     |     |     |     | 745 |     |     |     |     | 750 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | gtc | ctg | ggc | ggc | acg | ggc | tgg | gga | ttt | aaa | aac | atc | cgt | cgt | gga | 2304 |
| Ile | Val | Leu | Gly | Gly | Thr | Gly | Trp | Gly | Phe | Lys | Asn | Ile | Arg | Arg | Gly |      |
|     |     |     |     | 755 |     |     |     |     | 760 |     |     |     |     | 765 |     |      |

|     |     |     |     |
| --- | --- | --- | --- |
| agg | tcc | gga | ggg | gcc | taagtgccac cctgctccct ccgagcctgg cacccaccat | 2359 |
| Arg | Ser | Gly | Gly | Ala |
|     | 770 |

| | |
|---|---|
| ctcggccctg aaccacgagg ctgcctccac cctgccacag agggaggcac cgtgcaaatg | 2419 |
| tcttccgggt ccgaaccctt caactcctgg ctgcacaggg gttggggtt gggactgtga | 2479 |
| tatcgccttt cagaccacct gggtagaggg gccgggagga ggacgcttcc tgcccagttc | 2539 |
| cccatcccac tcatgcggc tttggccttg cacacgtctc cccctgtgaa tgtagcctcc | 2599 |
| atcatcacag actgccacag ctcacgttgg ggcctggacc ggtgcctggt ggggacagct | 2659 |
| gggtggcccc tcttcaaaac caggcagctg gaaccagggg agtagctccc ctggacctca | 2719 |
| cgggaagggg ctgatctaca ttttctctct ctcncncncn cncncncncn cncctctct | 2779 |
| ctctctctcc ctctttctct ctctcttct ctctctctct tttgttttac tacttaatct | 2839 |
| taactgatga atgtaacctt tggggttgctt ggggccaggg ggcaattgta gggatgtttt | 2899 |
| gacacttaca ggagggcctc ctggcccgag gccttgagac ctcccacatc cctccctggg | 2959 |

-continued

```
aggcccaaac gaatcctgtc agggaaccca gctggggcag ggcagccctg cttgccccca    3019
cctctgccca gcttagtaga agtcagagtg ctgattcaaa ccaaagctgc ctgtccngtg    3079
cccactgcct agctcatgac tctgtcccag actgtcttcg attccaaact gaccatcctg    3139
tccctgccag ggtgcatgca ttcgggggta tagaaaaata tagtccctaa aataaaactc    3199 caccttttccc ctttc                                                    3214
```

<210> SEQ ID NO 4
<211> LENGTH: 773
<212> TYPE: PRT
<213> ORGANISM: Mus musculus

<400> SEQUENCE: 4

```
Met Arg Arg Leu Arg Arg Trp Ala Ile Ala Ala Leu Leu Leu Pro
1               5                   10                  15

Leu Leu Pro Pro Gly Leu Gly Ala Leu Gly Pro Arg Gly Ala Leu
                20                  25                  30

His Trp Arg Ser Ser Ala His Val Gly Ser Pro Glu Ser Pro Gly
            35                  40                  45

Ser Glu Val Thr Glu Pro Ser Arg Leu Val Arg Gln Ser Ser Gly Gly
50                  55                  60

Glu Val Arg Lys Pro Gln Leu Asp Thr Arg Val Arg Gln Asp Pro Pro
65                  70                  75                  80

Arg Gly Thr Pro Val His Leu Ala Gln Val Ser Phe Val Ile Pro Ala
                85                  90                  95

Phe Asp Ser Asn Phe Thr Leu Asp Leu Glu Leu Asn His His Leu Leu
                100                 105                 110

Ser Ser Gln Tyr Val Glu Arg His Phe Ser Arg Glu Gly Thr Arg Gln
            115                 120                 125

His Ser Thr Gly Ala Gly Asp His Cys Tyr Tyr His Gly Lys Leu Arg
130                 135                 140

Gly Asn Pro Gln Ser Phe Ala Ala Leu Ser Thr Cys Gln Gly Leu His
145                 150                 155                 160

Gly Val Phe Ser Asp Gly Asn Leu Thr Tyr Ile Val Glu Pro Lys Glu
                165                 170                 175

Ile Ala Gly Pro Arg Gly Pro Pro Gln Gly Pro Leu Pro His Leu Ile
            180                 185                 190

Tyr Arg Thr Pro Leu Leu Pro Ala Pro Leu Gly Cys Arg Glu Pro Gly
            195                 200                 205

Cys Leu Phe Ala Val Pro Ala Gln Ser Thr Leu Pro Asn Trp Pro Lys
210                 215                 220

Leu Arg Arg Lys Arg Gln Val Arg Arg Gly His Pro Thr Val His Ser
225                 230                 235                 240

Glu Thr Lys Tyr Val Glu Leu Ile Val Ile Asn Asp His Gln Leu Phe
                245                 250                 255

Glu Gln Met Arg Gln Ser Val Val Leu Thr Ser Asn Phe Ala Lys Ser
            260                 265                 270

Val Val Asn Leu Ala Asp Val Ile Tyr Lys Glu Gln Leu Asn Thr Arg
            275                 280                 285

Ile Val Leu Val Ala Met Glu Thr Trp Ala Asp Gly Asp Lys Ile Gln
290                 295                 300

Val Gln Asp Asp Leu Leu Glu Thr Leu Ala Arg Leu Met Val Tyr Arg
305                 310                 315                 320

Arg Glu Gly Leu Pro Glu Pro Ser Asp Ala Thr His Leu Phe Ser Gly
                325                 330                 335
```

-continued

```
Arg Thr Phe Lys Ser Thr Ser Ser Gly Ala Ala Tyr Val Gly Gly Ile
            340                 345                 350
Cys Ser Leu Ser Arg Gly Gly Val Asn Glu Tyr Gly Asn Met Gly
        355                 360                 365
Ala Met Ala Val Thr Leu Ala Gln Thr Leu Gly Gln Asn Leu Gly Met
    370                 375                 380
Met Trp Asn Lys His Arg Ser Ser Ala Gly Asp Cys Lys Cys Pro Asp
385                 390                 395                 400
Ile Trp Leu Gly Cys Ile Met Glu Asp Thr Gly Phe Tyr Leu Pro Arg
                405                 410                 415
Lys Phe Ser Arg Cys Ser Ile Asp Glu Tyr Asn Gln Phe Leu Gln Glu
            420                 425                 430
Gly Gly Gly Ser Cys Leu Phe Asn Lys Pro Leu Lys Leu Leu Asp Pro
        435                 440                 445
Pro Glu Cys Gly Asn Gly Phe Val Glu Ala Gly Glu Glu Cys Asp Cys
    450                 455                 460
Gly Ser Val Gln Glu Cys Ser Arg Ala Gly Gly Asn Cys Cys Lys Lys
465                 470                 475                 480
Cys Thr Leu Thr His Asp Ala Met Cys Ser Asp Gly Leu Cys Cys Arg
                485                 490                 495
Arg Cys Lys Tyr Glu Pro Arg Gly Val Ser Cys Arg Glu Ala Val Asn
            500                 505                 510
Glu Cys Asp Ile Ala Glu Thr Cys Thr Gly Asp Ser Ser Gln Cys Pro
        515                 520                 525
Pro Asn Leu His Lys Leu Asp Gly Tyr Tyr Cys Asp His Glu Gln Gly
    530                 535                 540
Arg Cys Tyr Gly Gly Arg Cys Lys Thr Arg Asp Arg Gln Cys Gln Ala
545                 550                 555                 560
Leu Trp Gly His Ala Ala Asp Arg Phe Cys Tyr Glu Lys Leu Asn
                565                 570                 575
Val Glu Gly Thr Glu Arg Gly Asn Cys Gly Arg Lys Gly Ser Gly Trp
            580                 585                 590
Val Gln Cys Ser Lys Gln Asp Val Leu Cys Gly Phe Leu Leu Cys Val
        595                 600                 605
Asn Ile Ser Gly Ala Pro Arg Leu Gly Asp Leu Gly Gly Asp Ile Ser
    610                 615                 620
Ser Val Thr Phe Tyr His Gln Gly Lys Glu Leu Asp Cys Arg Gly Gly
625                 630                 635                 640
His Val Gln Leu Ala Asp Gly Ser Asp Leu Ser Tyr Val Glu Asp Gly
                645                 650                 655
Thr Ala Cys Gly Pro Asn Met Leu Cys Leu Asp His Arg Cys Leu Pro
            660                 665                 670
Ala Ser Ala Phe Asn Phe Ser Thr Cys Pro Gly Ser Gly Glu Arg Arg
        675                 680                 685
Ile Cys Ser His His Gly Val Cys Ser Asn Glu Gly Lys Cys Ile Cys
    690                 695                 700
Gln Pro Asp Trp Thr Gly Lys Asp Cys Ser Ile His Asn Pro Leu Pro
705                 710                 715                 720
Thr Ser Pro Pro Thr Gly Glu Thr Glu Arg Tyr Lys Gly Pro Ser Gly
                725                 730                 735
Thr Asn Ile Ile Ile Gly Ser Ile Ala Gly Ala Val Leu Val Ala Ala
            740                 745                 750
```

```
Ile Val Leu Gly Gly Thr Gly Trp Gly Phe Lys Asn Ile Arg Arg Gly
        755                 760                 765
Arg Ser Gly Gly Ala
    770

<210> SEQ ID NO 5
<211> LENGTH: 32
<212> TYPE: DNA
<213> ORGANISM: Artificial
<220> FEATURE:
<223> OTHER INFORMATION: primer

<400> SEQUENCE: 5
ttctgcggcc gcccagaccc tgtcccagag gt                              32

<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
aaggtcgact gcagcccctg gcatgtagag agt                             33

<210> SEQ ID NO 7
<211> LENGTH: 3830
<212> TYPE: DNA
<213> ORGANISM: Mus musculus

<400> SEQUENCE: 7
aagcttgact ggagcctgca ggtcctggag ccagcagccc cgtgcctggg ggagccagca    60
gcccagtgct gggatagggc tgggcttgct tgatctggcg ctcccctctg agcgtgaaca   120
gttgggccag ccaacatgc cttagtgtct gaagtctcaa ctatctccca ccacctatac    180
agagtctcac aagtctgccc ctccccattt tgtcccttc cccatgctcc accctcagg     240 cctcactggt cttctctgtg tcccttggag aagggtggtg tgtcccacag ctgagcctca   300
ctggctgcag gaaactggag aaagagagcc ctagcacatc tctcactgct gtctattggt   360
ccctgctttc ccattgtcag aaggaaaatg cggggctcac ggaggcttct ccatcatccc   420
taaggttgca caacttagaa gtggatcaaa ggaagggct tagaaagcta cttctccgag    480
tagccaggat agggacaagc aggggcagtc ctgaggtggg cagggcagag gtacccaggc   540
agagctgatg gagagagggc cagagccagg ccaggcatgg gggtggggt ggggacagc     600 agacttagcc aggttgaggg cgagggaggg gggttgtagc agggactcgt tgcccttgat   660
attctattct gagcctgatc gatgctctgg gggcttaggg tggggcttgg aacctcagac   720
agcctgggat ggggtgaatc tatgtccttg gggctcacag gtctgccttc acaggccctg   780
gcctttggtt ccacattgtc tgcatcccct ccccaccca cccacccccc cccaccccg     840 cggctcccat ggccgtgggc tgacttccat tcttgtcaac tttccagaag aaaaggcttg   900
ggagtatatt ccctggggtc agcctctatt ttttttcttt taattttcct ctcttttctg   960
tttggggtac aaggtctcag ccgccaggac agtatagaac tatggagccg aggctagcct  1020
cgaactcatg atcttcctgc ctcatcctcc tgggattgca gattgcatcc cccacacaag  1080
gcattaacct ctaacctgtg tggccttgtg ctttgctcgg gtctgtcagg aaggatggga  1140
accactggcc cacaaatatg gcagtgctca tagagttcag accactgcag gggccctaag  1200
cagtgcacag gaagaattag ttatagtaag gtgggagagg actcaactag gcatgggctc  1260
```

```
tgagacccgg tggcctgagt gtcaagggct ctctcttcct gcgaggaagg tctcttcctg    1320
caaggtgccc tcttcacacca gagagtagtc agccagccag tcctaaccag acttgctcca    1380
gaggcatctg gaggtctgtc ccctaagtaa atgggatagg agtaagactc tggcccctga    1440
attcaacccc agacatttct ttcctgtgct tgcaaatgat ttggaagacc aaagacttga    1500
ttgccaggat ttgaatggag gttgggctct agttgtatac ttaaagtggt tgtagctcag    1560
gctatccccc ctcccccttag cccaagctct gttaccccttc tggggggggg tatgtgaaac    1620
tttccctcca gcctttgatg tctccccttcc cccacccccca cctgccaggc agctgggcat    1680
ccaggcagag agggcagcca tgttgctcag gcctagtcca ttgccatagc aacttggagc    1740
ctcccagccc cgctgcatat gcccctttga aaaatttatc aggaaaactt ccgtgtttaa    1800
aaattaaccg ttggattgaa atattaaaga tgagctgctt tgggtaggca aagggcaatg    1860
gattgcgggg gagggggga cccctaccct cctgtcaagg tagcgcctgt ccttgcccag    1920
aatcggagcc ccagtggtca gtccccatgt gtctggaagc ccaagtcctc ctgggtagat    1980
tggggttggg gtagccaggg gcctgctccc cttcccttgt ccagccatga gctgagacct    2040 tctactttc catggtatgt ccgggggctt cattttgttc cactgaagct gggtggccct    2100
gtcaacagct ctgagagcct gacacaaggc cattgacaag tctaagctaa ccccttctct    2160
gtccctgatt ctcaaggaga ctaacccaga aagcagccag ggaacagagg gtgcccagga    2220
tctgggtggg gtgagtgggc tgtggccaag gttgaacaaa cagctctccc tgggaaagga    2280
gtctcaaaga caaggactca agaaaggggg ctcctcagct tctggggctt ggctgccccct    2340 tcccagggtg cctctgggt tccccactct cactcaggct gctcttcccc ttgccagcct    2400
gtgcacctgg cccaggtgag tttcgtcatc ccggccttcg actcaaactt cactctggac    2460
ctggagctga accagtgagt gtggcctgga gccagagggc agacagtggg catggctggc    2520
tgggggtact ggtggatgta gatccttaac taaggtggga cctaagcagg acttgctttc    2580
accgagtgac accccccttt cttcctgcta ctttgcgatt tcagtcacct cctgtcctcg    2640
cagtatgtgg agcgccactt cagccgggag ggaacaagac aacacagcac tgtgagtgtc    2700 tttgaaggg gtcaggtggg atagaggtgc tgttcggtga tcacagaggc aagggtgggg    2760
ctgtaggtgt gacgcagttg tagagagcct gacatgacac cagcagagag gaacactgaa    2820 gacgagaga cggatggctg gcgaaggggt atcaaggcta cactcagcat ggtcaggtgt    2880
ctggaaagtc cccacccctc cccgccttga agggcctgca gttaggaagg acagactggg    2940 tgtgtgggc cctgagcccc accccttgca tttgggtgct ttattatgtc cccttagctt    3000
tagaagggat agcaaccccct cccttgtttg gggagggctg gggaccatac tcagggtttt    3060
gggtacatcc taggctgaga gctccgctcc tgagcaccac ctccagacca aaatgtctcc    3120
tcttgttctg ggagtcccag atgcctggca cactagggtc ccagtcctgg aggccctgga    3180
gcctgaacaa agatgaatga gcgtctataa atagcttgcc ccccccccca caagcctgtt    3240
ctgtaactgg agcacaagta attctgcagg aagcggggtt gggagaggcg ggtgctgctg    3300
gtgtcctctg acctgtgagc aggtccggag aacccacgca cagttgtcca gctgcagacc    3360
acacgtgcct gtgagcttgt gtgtgagggg cgggggtgc atctacagca ggttctggtt    3420
aaatgacaca ctgtaggtgg catgctcagg acagggcctg gggtatggca ggtcctatgt    3480
aagagccagc tgttggtctc aaaggagtct gggatctgtt accagcctaa caaatagcca    3540
ggagctgctg ctgtggccta gtgtcctcat tttacggggc agatgaagct ggcccagaaa    3600
gtgttaagag cttgctcacg ggtgacagaa ccagcttaaa gccctagtgt tcctgagacc    3660
```

-continued

| | |
|---|---|
| tcagtccctc ccctgtactg tcctgctgcc tccatgctgg accaaggtgt cctgttcaca | 3720 |
| gcttttccca ctccacaggg ggctggagac cactgctact accatgggaa actccggggc | 3780 |
| aacccacagt cctttgctgc actctctaca tgccaggggc tgcagtcgac | 3830 |

```
<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
```

| | |
|---|---|
| aaggtcgacc ccttccccac ctcatttacc | 30 |

```
<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
```

| | |
|---|---|
| aagtcgacgt tcagggccga gatggtgggt gc | 32 |

```
<210> SEQ ID NO 10
<211> LENGTH: 6290
<212> TYPE: DNA
<213> ORGANISM: Mus musculus

<400> SEQUENCE: 10
```

| | |
|---|---|
| gtcgacccct tccccacctc atttaccgga cccctctcct cccagccccc cttggatgca | 60 |
| gggagccagg taagagaggg aaggggggtg gggctggacg gccgggcccc tcttacctac | 120 |
| tgttccccac aggctgcctg tttgctgtcc ctgcccagtc tgctctcccc aactggccca | 180 |
| agctaagaag gaaaaggcag gtacgggggcc cgcacagcct cgggctgcaa gaccttagag | 240 |
| atggtccaag gcaggtcatc ccctcctatg gctgggcaaa ggagagctca cagcgatgag | 300 |
| gtcaggggcc agggaactat ctccagaaag agtcccctca actcctccct agaactggtg | 360 |
| tctacacagg tccccatttt ggggtcctct gctctcattt ccaggctggg agggatggta | 420 |
| tttcctggcc agttggggggc tggcaccatc cctgactggg gacgagaatg ccccctcccc | 480 |
| acaagtctgc ccatggtttg ctcatggagg ggactgattc caagtgccta cccgccctcc | 540 |
| aggtccgcag gggccacccc acagtgcaca gcgagaccaa gtatgtggag ttgattgtaa | 600 |
| tcaatgacca ccagctggta agttcccggg ctaaggggggg accctgggat gaggggcccg | 660 |
| ggggagcctt gccttcttac cccacctttc tctcggcagt tgagcagat gcggcagtca | 720 |
| gtggtcctca ccagcaactt tgcaaaatct gttgtgaacc tggcagatgt ggtaagcacc | 780 |
| gtccctactc ccctctccct ctcccccaca tgcaggcatc caggagtcat tgtcagtcac | 840 |
| tgaccccccc ctcccccac ttcttggaaa tatagattgc agcctccctc cagcccctcc | 900 |
| cccatcttct ctctgggccc agatatacaa ggaacagctc aacacaagaa ttgttctggt | 960 |
| tgccatggaa acgtgggcag atggggacaa gatccaggtg caggatgacc tactgggagac | 1020 |
| cctggcccgg cttatggtct accggcggga gggtctgcct gagcccagtg atgccaccca | 1080 |
| cctcttctcg tgagtcccca cactgtaccc tgccagcttt gctggctgc tagttcttac | 1140 |
| cgcctgtgcc aggcgatctt ttcggggacc ctgcaggtgg agctcacctg ccacctgcca | 1200 |
| cctgcttcca gccacatgca ccagctgggt atcctctgca cctttgggctg tgcagggaat | 1260 |

```
gtgctctttg cctttctctg ccaggctgcc cgtcacccct tctttggtga tgaagtaccc   1320
tagtgatgga caaacccaat taaaggccct gaaacctcca tttggcttac gggtgaatga   1380
acccaaatag gggaagggct ggcctgaggc caccaggctg atagaaaggt ctggaaccca   1440
ctgctccttt gacatcatcc tgaccactct ctcccttcta ggggtagaac cttccagagc   1500
accagcagcg gggcggccta cgtgggaggc atctgttcac tgtcccgggg tggaggtgtg   1560
aacgaggtga gcacccagag gcccagccag gacagaggct tgctaagacc cagtgactgt   1620
tgggagcatg cagacatcct gtgctctgtc ttgcccatcc ctagtatggc aacatgggtg   1680
ccatggcggt gaccctggcc cagacgctag ggcagaactt gggcatgatg tggaataagc   1740
accggagctc agcaggtacc aacaaccctc ccagacccac acagagcctc aagaaatgaa   1800
gaaggggcca gtgggggtgc ttctccactc tatatctcat gtgttcttaa atctcctctt   1860
aggggactgc aagtgtccag acatttggct gggctgcatc atggaggaca ctgggtgagt   1920
tttggagaca gactttggga aggggtttggg gtaagaagag ccttcgagg agcactaaca   1980 gtcaagatgg gtggcttcaa gaggacctag ctcacaggac tactcaggat aaccaagaat   2040
ataggttatc tgtaaatagc tcagggatgc ttgggtacca aaaactgcca gactgcaggg   2100
cgcactctgg ccactgggag gcgctcgagc ctcgtgcgag gcgccgtccc tcccaggcgt   2160
tccgacactg ggctctttgt cccgaggttc aggagaaaga acgcaagcga cgtcctccac   2220
ccattcctag acaggagtat gggattgatt gtcgtgcaac ctcagggcag tccttcggtc   2280
tccttgtagt agtaaccaag tctctcgagg aagggctgtc cccagcaaca cagttcccct   2340
ctcgcccgtc taggttctat ttgccccgca agttctcgcg ctgcagcatc gacgaataca   2400 accagttttct gcaggaggga ggcgggagct gcctgttcaa caagcccctc aaggtactag   2460
cgcggagaac ggggaagcgg ggggtgggca gggtgccagc caggctcccg acatcccctc   2520
tccctccagc ttctggaccc tcccgagtgc ggaaacggct tcgtggaggc gggagaggag   2580
tgcgactgcg ggtcggtgca ggtgagcgct cctggtgggc tcccgtctgg gcccgggacg   2640
cgcgcatggg ctccgggaag ggagaataca gagtgggaag gggctagccc gcctctccac   2700
ttctccccgc gaccctcagg agtgcagccg agcagggggc aactgctgca aaaaatgcac   2760
cttgacgcac gacgccatgt gcagcgatgg gctctgttgt cgccgctgca aggtgaggac   2820
ctagcgagcg ggaggcgggg ggcggggaa gaagcaaaga aacgattgga tgccctcgat   2880
aagaggcggg aatggggaag agctgagtct gtttgggcgg gccttgtccc gaagagagcg   2940
ccaatgggga atgagttagg agctgaggac cggaggggga agtcacccctt actgctgagg   3000 gtggagaggg acaggaaatg agaatcaggc cttgggaccc acgttccagc acattaaccc   3060
tggaagggca gtggggaaat atttatcctt cccagaaaca catgcatgct tttcctagta   3120
tgagccacga ggtgtctcct gccgagaagc ggtgaatgag tgtgacattg cagagacctg   3180
caccggcgac tcaagccagg tctgccaaac catctgttct gtgggagctc aaagcaagac   3240 agcccctcc cttataagtt tggcgctgaa gagttgacta ctctgtgtgt cctctctgct   3300
tagcgggtgg ggtagccgca gctgaccagc ctcagctttt tcttctctga gaaagggtc   3360 tttcgagcca cctacctctg ttcggtcaat cattaaataa gcatttgtag tgacactggt   3420
attcctaccg cctgcccagt gtctagtgta ttctaaggat ctggtggatc gtaacatggg   3480
ttaactaggg cttctggggt aatggatgca agaaactggg gaagcttgga aaagctagga   3540
gacttaccag tcaaatccac agagccaaac aggcccccat ctttcgtgtg gaagagccat   3600
gtgacatgtg gccccttggg ggtagctttt ggttccttgc attctccccc cacccccccc   3660
```

```
cacacacacc ccgaacctca gctcagctct gggctaccct gctcagccag cctctctctc    3720
tctctctctc tctccagtgt cccccctaacc ttcacaagct ggacggttac tactgtgatc   3780
atgagcaggt atgagggata ggggtggggt ccttccgtcc gaattcagtg cagtcttgtc    3840
tccctcagtg tcttgatgct tcctctccca cggctcatag ggtcgttgct atggaggccg    3900
ctgtaaaacc cgggaccggc agtgccaagc cctatggggc catggtgagt ccagagactc    3960
gggaaaaccc aaagctcaga gttaggctgg gacgctggtt gaaggagcaa gccctgcaac    4020
caacgtggct tctgaagacc ttaggcatca agcctaagga ttaggcccaa gttttagagg    4080
tgcaggtctg aggtcctaga tgggatccag ggatctgtgg ggtgatgctt cctctctctc    4140
tttctctctc tagcggctgc ggatcgtttc tgctatgaga agctgaacgt ggaggggaca    4200
gagcgtggaa actgtggacg caagggatct ggttgggtcc agtgcagtaa gcagtaagta    4260
gcatccccgc cccagggtca gggaatctcc agaggtaaag gcagggctct aggaagagcc    4320
tgtgaggcca gaggggaagg agcaggctcg gtacttgggt ctacagagaa atttggcttc    4380
atcgacccca tgtgtcccta cagggatgtg ctctgtggct tccttctgtg cgtcaacatc    4440
tctggagctc cgcggctagg ggatctgggg ggcgacatca gcagtgtcac cttctaccac    4500
cagggcaagg agttggactg caggtgttgt ctggaaccgt ggatggggag gttaagggga    4560
caactgtgat ggggactaga ggacaggggt tgaggctgtg tataccatct ctccagggga    4620
ggccacgtgc agctagctga tggctcggac ctgagctatg tggaggacgg cacggcctgt    4680
gggcccaaca tgttgtgcct agatcaccgc tgcctgccag cctctgcctt caacttcagc    4740
acctgccctg gaagtggaga gcgaaggatc tgctcccatc atggggtggg tgtctggagg    4800
ccagggggag cctgctggag gaggctcaca cggagatgtg gccttgctta tccatgctgg    4860
cctcgcctac ctgtaggttt gcagcaacga ggggaagtgt atctgtcagc cagactggac    4920
aggcaaagac tgcagtattc acaacccact gcccacgtcc cctcccactg ggagactga    4980 gagatacaaa ggtgaggctg aagttgccca gcactgtcta tgttgcccgt tttccatgct    5040
tgtccctgcc aaccaagccc taccctcctc cccaggtccc agcggtacca acatcatcat    5100
tggctccatc gccggggctg tcctggtcgc agccatcgtc ctgggcggca cgggctgggg    5160
atttaagtaa gagacacatg ctccctagat cccccaacag gtgcttgggg gttcggcacc    5220
ctagactgtt ggagcctaat ggcctccctg acaggttagc tcaccctgaa ctcacacatc    5280
actcattcaa gccagcccac gggtcttgtt tgaacagttc aagaaactat ctactcatat    5340
ctaaacacca gactttacgg gaacaacctt gactcccagc ctcctgaaga ctgctcaacg    5400
catcccagca cggcctaggg cttgtctgag atgtctcccc gtccctatcc acattcagcc    5460
caggaactcc agaacgttgc agttagggtc tggtgtagcc cccacgttgg gcgcttgaag    5520
agccctgagg cccaaggtca caatgtgact tagtggccaa gctaggattt gaaccccta    5580 ccaagctggg atagatctcc acggtccatt tatgggacag gtcttcctgg gctgaaggc    5640 cgttcttttg gagaacagga ggttcacgca atttcttttt cctatctctc ttgcctgtcc    5700
tctccttggc tcctgaagaa acatccgtcg tggaaggtac gacccgaccc agcaggggc    5760 agtgtgatgc cggccacgtc atccctcccg ctgtccttgt ctccatttca tccgtccctt    5820
tgcattctgt tgaccgggag ctgggaccga tccgattccc gaagccctgc agggagcctg    5880
ggaagcgagt cctctgtctg ctcaggccct tcctcctgcc cacccgcctg ttgggccctg    5940
gcccaccttc atctgtcctt tctgccgccg ggtcccatgg ccgggtgggc gctggaactg    6000
tgccctgcaa cccctttccgc taggagggggg cctccccctg cgtcctgccc atctgttttg    6060
```

```
tctaccatgc caccgctgtc tgacctctgc cagaaccccc acctggccag cttgtgactt    6120
gatgcctcca ggacctctgg ggaggagcgg ggcaactaga gggctcaccc tcagagccca    6180
gcctcaagtc ctctcctgat gccctctctc cattccaggt ccggaggggc ctaagtgcca    6240
ccctgctccc tccgagcctg gcacccacca tctcggccct gaacgtcgac               6290
```

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11

```
ggacccggaa gacatttgca cggt                                              24
```

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12

```
tcgtgcttta cggtatcgcc gctcccgatt                                        30
```

<210> SEQ ID NO 13
<211> LENGTH: 2054
<212> TYPE: DNA
<213> ORGANISM: Artificial
<220> FEATURE:
<223> OTHER INFORMATION: probe

<400> SEQUENCE: 13

```
ggatccgccc aggggacgg tgagtgaggc tggggtgag gccaggggac tggagcaggc        60
ctcacagccc acaacagtcc gccaagtagg caggggttagg tgccaccgc tgaggtcgca     120 ccttaccgca gcttcccttt ctgtgtaatg ggccatcagg tggggctggt gcccaacagt     180
aagaacaccg ggactctcca gctccgggac tatccagctc cgggcccctc ccctgccgtg     240
cacaccagta gacactggca tgctccggtt tcagtttgct tgggtcatcc ttcaaccacc     300
tcccactgcc caccagaaac agtggttctg cctaaaacag gtcttgaggg acaggatagc     360
accctgcagt cagggattca tgctctgatg acccaccaaa ggcacccctc agtggacttt     420
tcttggaaca gcgtgatgtt tactcctgcc tcagtttccc cgctgtgcac acacaggctt     480
atccttcttg ccctagctga agttggggcc ttgcagaatg acctgaggcc caggattcat     540
cttcaaattg ccagctctac ctgtgcctgc tctgtcccct ccatactgct gggcccctgt     600
ccccgtcccc cccccccca gaggaaggtt aggaatgaag gagattaagt gcaattaata     660
attaattaat atcatgtgaa taatagccat ccagatggaa tcgtcattgg gcatgcctta     720
gcactccggg agcttggagc ccaaagttag ccaggccaac ctgggcggca gagggctgga     780
cacctggcag acacaggagg tgtagagaga ctcaaaggag gggcaaagcc aagtctgaga     840
agtttggggc agctggggagt ggtgggaggt aaactgggct gcgtagaggg aggagaggaa     900
gggaggagac tggcgtctgg ccctgcctaa tgtacttggt taaaagccct taaggggggag   960 gggaggagaa ggtagttggg cggtgcaggg atggggaata gttgagaatg gagtggagca    1020
ggaaggagca tgcataatgg atggaccatc actcagggct gtgttgagga ggggagggga    1080
gggggctaat ggtcctgagt tggcagctgc tgcaggggta gggatggggc tagagatcaa    1140
```

```
cttcagcgcc cactccagca cccagggaat cagctgaatg agccttgggg atgtcccagg    1200
cccaggggtt gggtatcctg gttgcactat ggtccctagc gtagctttct atgaactgtg    1260
aactccgcag cgcacttggc cctgcctgac agtctctggc tggagcttcc cagggtgtat    1320
gtacatacta tgggatcaag gtatagttga gaagcacaag ggatgggggg gttaggggct    1380
ctagctccgt aggctgtgac ttctgctagc tcttcctcag gacagcaggc ctgggctgtg    1440
ggcagaaaag ctgtagggct gagctggctt ctttggatgc tgttcttttg ggtggatgtg    1500
ttggcttgtg tgtggagcca ggtaagcaag tgactgaatc caacacctaa gaagtggcca    1560
aggcacgggg tgagagttct gtagatcggg gctgtgcttg tttcctgttg tttctctagg    1620
cctgagaccc cccttaggga cctcatgcat cttcccccag gagaaccact tggcactctg    1680
gtgtccccat cccttaggtg ccaaaggcag gagacctgtt caggtggtaa aggctgcgaa    1740
ggccatgggg ctgctttggg tcaggcactc tgtgtacctt tacatccgtt tctttccaca    1800
aggccatagg cagatacttc tgtctgcccc tctgcagatc agccagctca gatccagaga    1860
acctaagcca cttgccaggt taatagacct tcagcggtca caggaatagt gttcccctc     1920 aagcccaggg cactttccac tggacggttc tgcctctaga gattttgaaa tttaggccca    1980
agagacaata tctccaactc tcccccaagt caaagacgga agagcagagg agatcagtac    2040
atgtcgaaga attc                                                     2054
```